United States Patent
Geier et al.

(10) Patent No.: US 11,965,873 B2
(45) Date of Patent: *Apr. 23, 2024

(54) PARALLEL PLATE CAPACITOR SYSTEM FOR DETERMINING IMPEDANCE CHARACTERISTICS OF MATERIAL UNDER TEST (MUT)

(71) Applicant: TransTech Systems, Inc., Latham, NY (US)

(72) Inventors: Manfred Geier, Oakland, CA (US); Adam D. Blot, Altamont, NY (US); Andrew J. Westcott, Troy, NY (US)

(73) Assignee: TRANSTECH SYSTEMS, INC., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,018

(22) Filed: Feb. 15, 2023

(65) Prior Publication Data

US 2023/0194498 A1   Jun. 22, 2023

Related U.S. Application Data

(63) Continuation of application No. 17/307,114, filed on May 4, 2021, now Pat. No. 11,592,432, which is a
(Continued)

(51) Int. Cl.
*G01N 33/24*   (2006.01)
*A61B 5/0536*   (2021.01)
(Continued)

(52) U.S. Cl.
CPC ......... *G01N 33/246* (2013.01); *A61B 5/0536* (2013.01); *G01N 27/223* (2013.01);
(Continued)

(58) Field of Classification Search
CPC .. G01N 33/246; G01N 27/223; G01N 33/383; G01N 27/026; G01N 33/24;
(Continued)

(56) References Cited

U.S. PATENT DOCUMENTS

| 3,782,179 A | 1/1974 | Richards |
| 9,494,538 B2 | 11/2016 | Kozicki et al. |

(Continued)

FOREIGN PATENT DOCUMENTS

| EP | 2693206 A1 | 2/2014 |
| GB | 1177983 | 1/1970 |
| WO | 2018045593 A1 | 3/2018 |

OTHER PUBLICATIONS

PCT International Search Report and Written Opinion for International Application No. PCT/US2019/028678, dated Jul. 26, 2019, 8 pages.

(Continued)

*Primary Examiner* — Raul J Rios Russo
(74) *Attorney, Agent, or Firm* — Hoffman Warnick LLC

(57) ABSTRACT

Various aspects of the disclosure relate to evaluating the electromagnetic impedance characteristics of a material under test (MUT) over a range of frequencies. In particular aspects, a system includes: an electrically non-conducting container sized to hold the MUT, the electrically non-conducting container having a first opening at a first end thereof and a second opening at a second, opposite end thereof; a transmitting electrode assembly at the first end of the electrically non-conducting container, the transmitting electrode assembly having a transmitting electrode with a transmitting surface; and a receiving electrode assembly at the second end of the electrically non-conducting container, the receiving electrode assembly having a receiving electrode with a receiving surface, wherein the receiving electrode is approximately parallel with the transmitting elec-
(Continued)

trode, and wherein the transmitting surface of the transmitting electrode is larger than the receiving surface of the receiving electrode.

19 Claims, 14 Drawing Sheets

Related U.S. Application Data continuation of application No. 16/640,157, filed as application No. PCT/US2019/028678 on Apr. 23, 2019, now Pat. No. 11,022,594.

(60) Provisional application No. 62/661,682, filed on Apr. 24, 2018.

(51) Int. Cl.
| | |
|---|---|
| *G01N 27/22* | (2006.01) |
| *G01N 33/38* | (2006.01) |
| *G01R 19/00* | (2006.01) |
| *G01R 27/00* | (2006.01) |
| *G01R 27/02* | (2006.01) |
| *G01R 27/32* | (2006.01) |
| *G01R 31/34* | (2020.01) |
| *G01R 31/50* | (2020.01) |
| *G01R 35/00* | (2006.01) |

(52) U.S. Cl.
CPC ....... *G01N 33/383* (2013.01); *G01R 19/0092* (2013.01); *G01R 27/00* (2013.01); *G01R 27/02* (2013.01); *G01R 31/50* (2020.01); *G01R 35/005* (2013.01); *A61B 2562/0217* (2017.08); *G01R 27/32* (2013.01); *G01R 31/343* (2013.01)

(58) Field of Classification Search
CPC .......... A61B 5/0536; A61B 2562/0217; G01R 19/0092; G01R 27/00; G01R 27/02; G01R 31/50; G01R 35/005; G01R 27/32; G01R 31/343
USPC ................................. 324/600–727
See application file for complete search history.

(56) References Cited

U.S. PATENT DOCUMENTS

| | | | |
|---|---|---|---|
| 9,804,112 B2 | 10/2017 | Pluta et al. | |
| 10,161,893 B2 | 12/2018 | Colosimo et al. | |
| 2005/0267700 A1 | 12/2005 | Gamache et al. | |
| 2011/0239757 A1 | 10/2011 | Camenisch | G01F 23/268 73/304 C |
| 2012/0245873 A1 | 9/2012 | Donnangelo et al. | |
| 2012/0319704 A1 | 12/2012 | Skaling | G01N 33/246 324/658 |
| 2014/0278300 A1* | 9/2014 | Lipowitz | G06F 30/20 703/2 |
| 2015/0054512 A1* | 2/2015 | DiFoggio | E21B 49/088 324/324 |
| 2015/0137831 A1* | 5/2015 | Pluta | G01R 33/323 324/647 |
| 2015/0241362 A1 | 8/2015 | Kobayashi et al. | |
| 2016/0020599 A1 | 1/2016 | Harper | G01N 27/023 219/209 |
| 2016/0054247 A1 | 2/2016 | Colosimo | G01N 27/026 324/629 |
| 2017/0030852 A1 | 2/2017 | Portmann | G01N 27/223 |
| 2018/0011040 A1* | 1/2018 | Pluta | A61B 5/0536 |
| 2020/0408708 A1* | 12/2020 | Geier | G01N 27/226 |
| 2021/0255161 A1* | 8/2021 | Geier | G01N 27/223 |
| 2021/0325326 A1* | 10/2021 | Blot | G01N 27/028 |

OTHER PUBLICATIONS

European Search Report for Application No. 19791879.0, dated Jul. 10, 2020, 11 pages.

Fuchs et al., "Investigation on the Dependency of of the Electrical Capacitance on the Moisture Content of Wood Pellets," 3rd International Conference on Sensing Technology, Nov. 30-Dec. 3, 2008, 5 pages.

Fuchs et al., "Using Capacitive Sensing to Determine the Moisture Content of Wood Pellets—Investigations and Application," International Journal on Smart Sensing and Intelligent Systems, vol. 2, No. 2, Jun. 2009.

* cited by examiner

PARALLEL PLATE CAPACITOR SYSTEM FOR DETERMINING IMPEDANCE CHARACTERISTICS OF MATERIAL UNDER TEST (MUT)

PRIORITY CLAIM

This application claims priority to U.S. patent application Ser. No. 17/307,114, filed on May 4, 2021, which itself claims priority to U.S. Pat. No. 11,022,594 (application Ser. No. 16/640,157), filed on Feb. 19, 2020, which itself claims priority to Patent Cooperation Treaty (PCT) Application: U.S. Ser. No. 19/28,678, filed on Apr. 23, 2019, which itself claims priority to U.S. Provisional Patent Application No. 62/661,682, filed on Apr. 24, 2018, each of which is herein incorporated by reference in its entirety.

TECHNICAL FIELD

This disclosure relates generally to material testing. In particular, this disclosure relates to determining impedance characteristics of materials over a range of frequencies.

BACKGROUND

In U.S. Pat. No. 7,219,024, a system is described for conducting electromagnetic impedance spectroscopy to non-invasively determine the in-place compaction (i.e., density) and moisture of various engineering materials, with specific interest in soils. The system uses an algorithm to relate the measured impedance of the soil over a frequency range to the compaction level (density) of the soil and the moisture level. In this conventional system, a user inputs the soil characteristics as determined by standard laboratory tests, which provide the plasticity limits (ASTM D4818, a standard issued by ASTM International, West Conshohocken, PA), particle size distribution (ASTM D422), and Proctor limits (ASTM D698 and D1557) of the soil. The algorithm then correlates the measured impedance over a range of frequencies to the compacted soil density and moisture level in the field. In order to make these correlations, the conventional system must develop a library of the impedance characteristics of soils with varying levels of compaction and moisture levels. Real-time calculations and correlations made by the system algorithm are predicated on this library.

In conventional approaches, the library is developed with a combination of testing procedures in the laboratory and in the field. The laboratory testing has limitations due to the size of the test fixture capable accommodating the compaction method, as well as the amount of soil required to perform an in-laboratory test. Additionally, it is difficult to reliably recreate field compaction results in a laboratory due to the methods of field compaction, control of the compaction variation with depth, the distribution of moisture, and other factors. While field testing is more accurate than laboratory testing in replicating field compaction methodologies, it is limited in terms of the type of soils that can be tested. Additionally, changes in weather conditions will inevitably limit the conditions of a field test. As examples, weather will affect variables such as the amount of precipitation in a sample, timing of the precipitation, ambient temperature, and amount and duration of direct sun exposure.

SUMMARY

All examples and features mentioned below can be combined in any technically possible way.

Various aspects of the disclosure overcome challenges in conventional approaches for developing a soil compaction library. In particular aspects, a material testing system and related method are disclosed, where the system is configured to conduct reliable material compaction testing across a range of frequencies. The system is configured to measure the impedance of a material over a range of frequencies with controlled amounts of moisture and compaction levels. In particular aspects, the system is configured to measure the impedance of small samples of material (e.g., soil) in a laboratory or other setting.

In particular aspects, a system includes: an electrically non-conducting container sized to hold the MUT, the electrically non-conducting container having a first opening at a first end thereof and a second opening at a second, opposite end thereof; a transmitting electrode assembly at the first end of the electrically non-conducting container, the transmitting electrode assembly having a transmitting electrode with a transmitting surface; and a receiving electrode assembly at the second end of the electrically non-conducting container, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode.

An aspect of the disclosure includes the preparation of the material under test (MUT) by compaction of the MUT (e.g. soils) within a cylindrical container as specified in ASTM Standard D4253.

Additional aspects of the disclosure allow for the placement of various types of materials that may be tested for their impedance characterization over a range of frequencies without first being subjected to the compaction process.

Additional aspects of the disclosure enable impedance characterization of materials over a range of frequencies. In some particular aspects, electromagnetic impedance characterization of a (MUT) is performed over a range of frequencies, e.g., using a parallel plate electrode geometry within a non-conducting container where an electrode in communication with the MUT transmits an electromagnetic signal over a range of frequencies through the MUT to a receiving electrode. The electrodes can be connected to a signal generator/analyzer which communicate the results to a computing device. The transmitting electrode has a conductive backer ground plate which acts as the back plane of the electrode and encloses a volume with the electrode. The receiving electrode has a conductive backer ground plate that extends from the front plane of the electrode and at least partially surrounds the electrode to enclose a volume with the electrode. The transmitting electrode size can be larger than the receiving electrode in order to control the electric field lines passing through the MUT from the transmitting electrode to the receiving electrode.

Various particular aspects of the disclosure relate to evaluating the electromagnetic impedance characteristics of a material under test (MUT) over a range of frequencies. In some particular aspects, a system includes: an electrically non-conducting container sized to hold the MUT, the electrically non-conducting container having a first opening at a first end thereof and a second opening at a second, opposite end thereof; a transmitting electrode assembly at the first end of the electrically non-conducting container, the transmitting electrode assembly having a transmitting electrode with a transmitting surface; and a receiving electrode assembly at the second end of the electrically non-conducting container, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode.

Additional particular aspects of the disclosure relate to evaluating the electromagnetic impedance characteristics of a material under test (MUT) over a range of frequencies. In some particular aspects, a system includes: a container that is lined with a non-conducting liner. The container and non-conducting liner are sized to hold the MUT, the container having a first opening at a first end thereof and a second opening at a second, opposite end thereof; a transmitting electrode assembly at the first end of the container, the transmitting electrode assembly having a transmitting electrode with a transmitting surface; and a receiving electrode assembly at the second end of the container, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode.

Additional particular aspects relate to a method for determining an electromagnetic impedance characteristic of a material under test (MUT). In some cases where the MUT is subjected to the compaction process, the method includes: with the compacted MUT (e.g. soil) in a testing system including: a container having a first opening at a first end thereof and a second opening at a second, opposite end thereof; and a transmitting electrode assembly at the first end of the container, the transmitting electrode assembly having a transmitting electrode with a transmitting surface, including having the MUT on the transmitting electrode assembly in the container; sealing a bottom of the container, placing a receiving electrode assembly at the second end of the container over the MUT, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode; transmitting a set of electromagnetic signals from the transmitting electrode, through the MUT to the receiving electrode; and determining a characteristic of the MUT based upon a change in the set of electromagnetic signals over a range of frequencies from the transmitting electrode to the receiving electrode.

Additional particular aspects relate to a method for determining an electromagnetic impedance characteristic of a material under test (MUT). In some cases where the MUT is not subjected to the compaction process, the method includes: placing the MUT in a testing system including: a container sized to hold the MUT, the container having a first opening at a first end thereof and a second opening at a second, opposite end thereof; and a transmitting electrode assembly at the first end of the container, the transmitting electrode assembly having a transmitting electrode with a transmitting surface, the MUT being placed on the transmitting electrode assembly in the container; sealing a bottom of the container; placing a receiving electrode assembly at the second end of the container over the MUT, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode; transmitting a set of electromagnetic signals from the transmitting electrode, through the MUT to the receiving electrode; and determining a characteristic of the MUT based upon a change in the set of electromagnetic signals over a range of frequencies from the transmitting electrode to the receiving electrode.

Further particular aspects include a method of assembling a testing system, the method including: placing a container, placing a material under test (MUT) in the container including a transmitting electrode; sealing a bottom of the container; and placing a receiving electrode at an end of the container.

Implementations may include one of the following features, or any combination thereof.

In certain cases, the transmitting electrode assembly further includes: a transmitting electrode backer ground plate at least partially surrounding the transmitting electrode, the transmitting electrode backer ground plate being electrically grounded and insulated from the transmitting electrode, wherein the transmitting electrode backer ground plate extends from a plane formed by the transmitting electrode and creates an electrically isolated volume proximate to the transmitting electrode. In particular aspects, the transmitting electrode backer ground plate is formed of an electrically conductive material and includes a recess corresponding with the transmitting electrode, and wherein the plane formed by the transmitting electrode is substantially parallel with a surface of the MUT.

In some embodiments, the receiving electrode assembly further includes: a receiving electrode backer ground plate at least partially surrounding the receiving electrode, the receiving electrode backer ground plate being electrically grounded and insulated from the receiving electrode, wherein the receiving electrode backer ground plate extends from a plane formed by the receiving electrode and creates an electrically isolated volume proximate to the receiving electrode. In certain cases, the receiving electrode backer ground plate is formed of an electrically conductive material and includes a recess corresponding with the receiving electrode, and wherein the plane formed by the receiving electrode is substantially parallel with a surface of the MUT.

In particular embodiments, during operation of the system, the transmitting electrode and the receiving electrode are in direct physical contact with the MUT and electrically non-conductive with the MUT.

In certain cases, the system further includes a signal generator/analyzer coupled with the transmitting electrode and the receiving electrode, the signal generator/analyzer comprising a generator component configured to initiate transmission of a set of electromagnetic signals over a range of frequencies from the transmitting electrode, through the MUT, to the receiving electrode, and an analyzer component configured to detect a change in the set of electromagnetic signals from the transmitting electrode to the receiving electrode. In some aspects, the system further includes a computing device coupled with the signal generator/analyzer, wherein the computing device is configured to determine a characteristic of the MUT based upon the change in the set of electromagnetic signals from the transmitting electrode to the receiving electrode, wherein determining the characteristic of the MUT comprises: determining a difference in an aspect of the set of electromagnetic signals over a range of frequencies; comparing the difference in the aspect to a predetermined threshold; and determining the characteristic of the MUT based upon the compared difference.

In particular embodiments, the transmitting electrode and the receiving are aligned in parallel with one another.

In certain cases, the container and/or the electrically non-conducting liner includes plastics such as polyester, polyethylene, polyvinyl chloride (PVC), polytetrafluoroethylene (Teflon), poly carbonate, and/or various fiber glass reinforce epoxy laminate materials (e.g. FR-4). In some cases, the container and/or the electrically non-conducting liner is formed of a poly methyl methacrylate (PMMA or acrylic), which is substantially transparent and allows for visual observation of the testing process.

In some aspects, the container or the liner has a cylindrical cross-section, rectangular cross-section, or oblong cross-section, taken in a direction perpendicular to a primary axis thereof.

In particular implementations, the container includes at least two distinct sections. In certain cases, the transmitting electrode has a diameter larger than an inner diameter of the container, and one of the at least two distinct sections comprises a seat for supporting an overhang portion of the transmitting electrode.

In particular implementations that include a container with an electrically non-conducting liner, the electrically non-conducting liner includes at least two distinct sections. In certain cases, the transmitting electrode has a diameter larger than an inner diameter of the container and one of the at least two distinct sections of the electrically non-conducting liner includes a seat for supporting an overhang portion of the transmitting electrode.

In certain embodiments, the transmitting electrode assembly and the receiving electrode assembly are shaped to coincide with a cross-sectional shape of the first opening and second opening, respectively, of the container.

In some aspects, the transmitting electrode assembly and the receiving electrode assembly are substantially contained within the container.

In particular cases, the transmitting electrode assembly and the receiving electrode assembly are sized to complement an opening in a soil compaction device.

In some aspects, a testing method can further include the measurement of solid materials that are not of a size or shape to fit within the container.

In certain embodiments, a solid material under test may be placed directly on the transmitting electrode assembly with the receiving electrode assembly being placed on top of the MUT and aligned with the transmitting electrode without an enclosing container.

In some particular aspects, a system for measuring an electromagnetic impedance characteristic of a material under test (MUT) includes: at least one electrically non-conducting support sized to physically support the MUT; a transmitting electrode assembly positioned on a first side of the MUT, the transmitting electrode assembly having: a transmitting electrode with a transmitting surface; and a transmitting electrode backer ground plate at least partially surrounding the transmitting electrode, the transmitting electrode backer ground plate being electrically grounded and insulated from the transmitting electrode, wherein the transmitting electrode backer ground plate extends from a plane formed by the transmitting electrode and creates an electrically isolated volume proximate to the transmitting electrode; and a receiving electrode assembly positioned on a second side of the MUT opposite the first side of the MUT, the receiving electrode assembly having a receiving electrode with a receiving surface, wherein the receiving electrode is approximately parallel with the transmitting electrode, and wherein the transmitting surface of the transmitting electrode is larger than the receiving surface of the receiving electrode.

In particular cases, the receiving electrode has a backer ground plate at least partially surrounding the transmitting electrode, the receiving electrode backer ground plate being electrically grounded and insulated from the receiving electrode, wherein the receiving electrode backer ground plate extends from a plane formed by the transmitting electrode and creates an electrically isolated volume proximate to the transmitting electrode.

In certain implementations, the MUT is a solid material, and an outer dimension of the MUT extends beyond an outer dimension of the at least one electrically non-conducting support such that the at least one electrically non-conducting support does not envelop the MUT.

In particular cases, the solid material includes a solid concrete sample or a solid asphalt sample.

In some implementations, the MUT includes soil.

In certain implementations, the MUT includes a granular material such grains.

In certain implementations, the MUT includes a liquid such as milk, oils, or other organic and inorganic fluids.

In some cases, the transmitting surface is configured to be placed in direct physical contact with the MUT, where the transmitting electrode backer ground plate is electrically conducting, and where the plane is formed by the rear surface of the transmitting electrode.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

BRIEF DESCRIPTION OF THE DRAWINGS

The embodiments of this disclosure will be described in detail, with reference to the following figures, wherein like designations denote like elements, and wherein.

Figure 1:
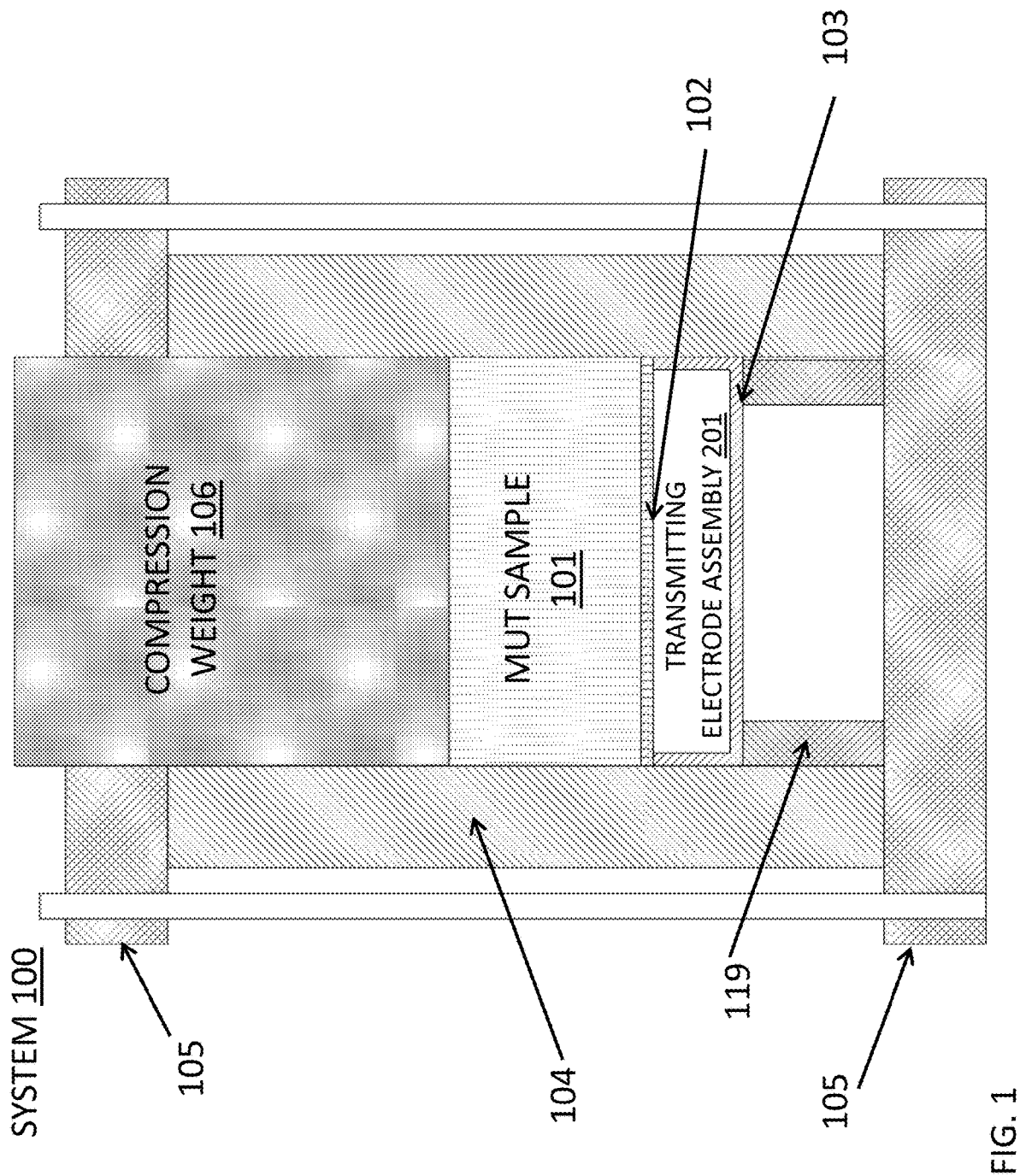
FIG. 1 shows a cross-sectional view of a system according to various embodiments of the disclosure.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

As noted herein, this disclosure relates generally to material testing. In particular, this disclosure relates to determining impedance characteristics of materials. In some aspects, impedance characteristics of materials are determined over a range of frequencies.

One approach disclosed according to embodiments includes modifying the (soil) compaction method described in ASTM Standard D4253 (standard issued by ASTM International, West Conshohocken, PA), to comply with the disclosed system including a parallel plate capacitor and an electrically non-conducting container. This approach can include placing a variety of materials with specific levels of moisture in the disclosed compaction device and compacting each of those material samples to different levels of compaction. After compaction, the compaction device is removed and a component of the disclosed parallel plate capacitor is placed on the surface of the soil sample. After placement of the parallel plate capacitor, electromagnetic signals are generated over a range of frequencies and transmitted through the material, and the impedance characteristics of the material sample are measured and stored.

The electromagnetic signals may be generated by any number of methods known in the art. For example, standard commercial instruments such as a Keysight network analyzer or impedance analyzer may be used. Also, the circuits described in U.S. Pat. No. 7,219,024 or U.S. Patent Application No. 62/434,789 (both of which are incorporated by reference in their entirety) may be used. While one method of material compaction is described by ASTM Standard D4253 (standards documentation hereby incorporated by reference in its entirety), other methods of material (e.g., soil) compaction are described in literature but are not codified in an ASTM Standard. One of these approaches involves use of a Gyratory Compactor, which is a conventional piece of laboratory equipment used for asphalt testing, and manufactured by companies such as Troxler Electronic Laboratories, Gilson Company, Humboldt Manufacturing, and Pine Test Equipment. Another device is the California Kneading Compactor, which is described in California Test 104 for soils and is manufactured by Forney LP. The Gyratory Compactor and California Kneading Compactor are automatic compacting systems. Additional tests can be performed, e.g., with a manual system, such as the Marshall Compactor. However, this manual system approach has various drawbacks when compared with the automatic compacting systems.

While the systems and testing approaches described herein are applicable to many materials, portions of the discussion will focus on applications to the electromagnetic characterization (e.g., over a range of frequencies) of controlled samples of soil of varying composition, moisture levels, and degrees of compaction utilizing a standard compaction method.

FIG. 1 illustrates a cross-section of a system 100 which is in compliance with ASTM Standard D4253. This system 100 includes a non-conducting cylindrical container 104 into which a material under test (MUT) sample 101 is placed. In various implementations, the MUT sample 101 includes a soil sample. A compression weight 106 is placed on top of the MUT sample (or simply, MUT) 101 to compress the soil. In some examples, the weight of compression weight 106 is determined to provide a compressive force of 2 lbs/in$^2$ (13.8 kPa) when combined with characteristics of the vibration device 107 (e.g., shaker table, FIG. 2), as specified in ASTM Standard D4253. However, in other implementations, the MUT 101 can include materials that can flow into the cylindrical volume. These can include, e.g., granular materials such as soils and grains, slurries such as fresh concrete, and liquids. System 100 can also be used to test solids that are configured to fit within a cylindrical testing apparatus.

There are other infrastructure testing specifications that may be used with the subject apparatus(es) disclosed herein. Specifically, a soil Proctor test (ASTM D698 and D1557) may be tested. For asphalt, the cores cut from finished roads (ASTM D1188, D3203, D3549, and D5361) may be tested as well as the asphalt gyratory samples (ASTM D3387, D6925, and D7229). Additionally, concrete cylinders which are collected and aged per ASTM C31, C39, C172, and C192 may be characterized with the subject apparatus.

While some of the description for this disclosure focuses on its use with soils, in other implementations, the MUT can include materials that can flow into the cylindrical volume, e.g., granular materials such as soils and grains, slurries such as fresh concrete, and liquids. For example, U.S. Pat. No. 10,161,893 ("Characterization of material under test (MUT) with electromagnetic impedance spectroscopy", filed as U.S. patent application Ser. No. 14/825,542, and herein incorporated by reference in its entirety) describes a system for the field use of electromagnetic impedance to characterize wet concrete as it is delivered to a construction site. The systems of the current disclosure may be used to secure the dielectric and impedance characterization of wet concrete to be used in the development of the algorithms for use with the system of U.S. Pat. No. 10,161,893. The systems disclosed herein may also be used in characterizing dielectric and impedance characteristics various organic liquids such as dairy products (milk), olive oil, fruits, other vegetable oils, cookies, pork and fish. The sensor system of the current disclosure may be used to secure the dielectric and impedance characterization of various liquids to be used in the development of the algorithms for the correlation with physical properties of interest for those liquids.

Referring to FIG. 1, flanges 105 are illustrative of one mounting mechanism for assembling the system 100, e.g., to maintain the position of compression weight 106 on MUT sample 101. In contrast to the conventional systems which use a fixed base supporting the compressed soil sample, system 100 includes a parallel plate electrode assembly which acts as the base of the test cylinder. This parallel plate (transmitting) electrode assembly 201 includes an electrode 102 and a (conductive) backer ground plate 103. The electrode 102 is supported by the backer ground plate 103, which is in turn supported by a non-conducting support member 119 (formed of any non-conducting material described herein). Additional aspects of a backer ground plate can be found in U.S. Provisional Patent Application No. 62/619,275, which is hereby incorporated by reference in its entirety.

Figure 2:
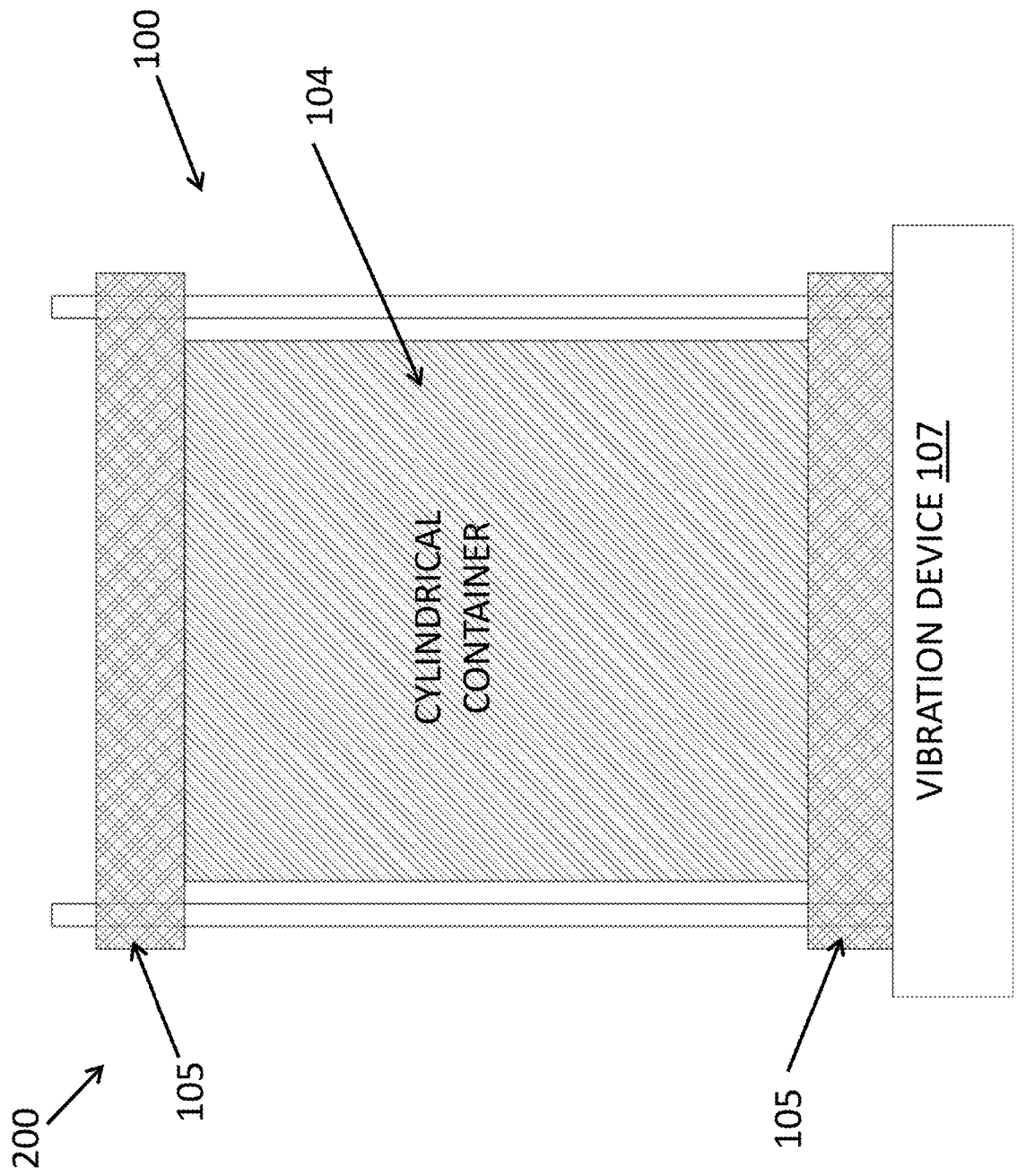
FIG. 2 shows a compaction fixture from FIG. 1 attached to a vibration device according to various additional embodiments of the disclosure.

FIG. 2 shows an assembly 200 including the system 100 mounted to a vibration device (also referred to as a shaker table) 107. Vibration devices such as shaker tables are well known in the art and various acceptable types are specified in ASTM Standard D4253.

The MUT sample 101 (FIG. 1) is selected to be either representative of a general class of materials (e.g., soils) as specified in ASTM Standard D2487, or a material sample from a specific location (e.g., soil from a construction site or other area of interest). In various embodiments, in the case of soil, the sample 101 is oven dried per ASTM Standard D4442. Various amounts of de-ionized water are added to the dry soil to provide for a test matrix of gravimetric water content which is defined as follows:

$$\theta_g = \frac{m_{water}}{m_{dry}} = \frac{m_{wet} - m_{dry}}{m_{dry}}$$

where $\theta_g$ is the gravimetric water content, $m_{water}$ is the weight of water added, $m_{dry}$ is the weight of the dry soil sample, and $m_{wet}$ is the combined weight of the water and dry soil in the sample. In order to adjust for the salinity of soil found naturally, sodium chloride (NaCl) can be added to the de-ionized water. In these cases, the impedance characteristic will be a function of the soil type, water content, salinity, and the degree of compaction.

The total volume of a soil sample, $V_{total}$, is made up of three components: the volume of the dry soil, $V_{dry}$; the volume of water, $V_{wet}$; and the volume of air, $V_{air}$. When soil is compacted, the volume of air is reduced, but the volumes of water and dried soil remain constant so that the total volume, $V_{total}$, is reduced. There is an optimum level of water content which produces the maximum value of dry density. This is referred to as the Proctor maximum and is determined by ASTM Standard Tests D698 and D1557.

The soil characteristics that are desired to be correlated to the impedance characteristics over a range of frequencies are the gravimetric moisture content and the dry density. The dry density is defined as follows:

$$\rho_{dry} = \frac{m_{dry}}{V_{total}}$$

where $\rho_{dry}$ is the density of the dried soil, $m_{dry}$ is the weight of the dry soil, and $V_{total}$ is the total volume of sample. The type of soil as defined by the ASTM classifications selected for testing and the masses of water and dry soil in the sample are determined in the test protocol specifications. The only variable that is changed is the compaction of the soil, which is a function of the change of volume achieved by the compaction and the reduction of the volume of air, $V_{air}$. Since the area of the compaction cylinder is known, the determination of volume depends only on the measurement of the height of the soil sample at various compaction levels. Thus, the volume is given by this relation:

$$V_{total} = A_{cyl} * H_{sample}$$

where $A_{cyl}$ is the internal area of the cylinder and $H_{sample}$ is the height of the soil sample at various levels of compaction. The height of the compacted MUT sample 101 may be measured by various means which are well known in the art. ASTM D4253 specifies use of a dial indicator to measure the compacted height. However, there are other known methods which provide a digital output and potentially better precision than the dial indicator.

An alternative approach for determining the height to the MUT sample 101 is to use a spacer or a stop to fix the height of the compaction process or the MUT sample 101.

Figure 3:
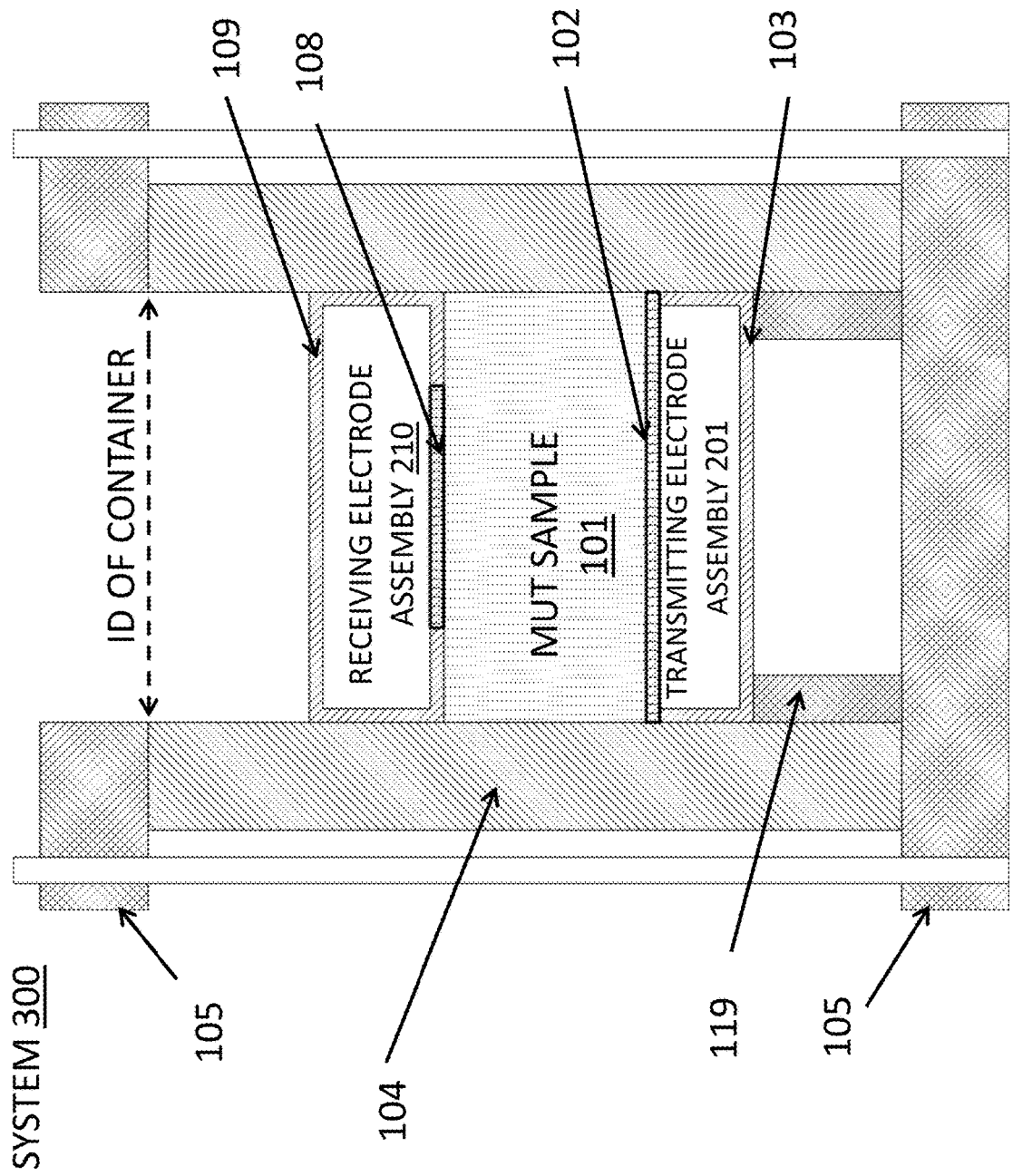
FIG. 3 shows a system according to various further embodiments of the disclosure.

Once the MUT sample 101 is compacted to a desired test level, the compressive weight 106 (FIG. 1) is removed and a second part of the parallel plate electrode assembly (receiving electrode assembly), as shown in system 300 in FIG. 3, is placed on the top of the compressed MUT sample 101. This receiving electrode assembly 210 includes an electrode 108 and a (conductive) backer ground plate 109.

Figure 4:
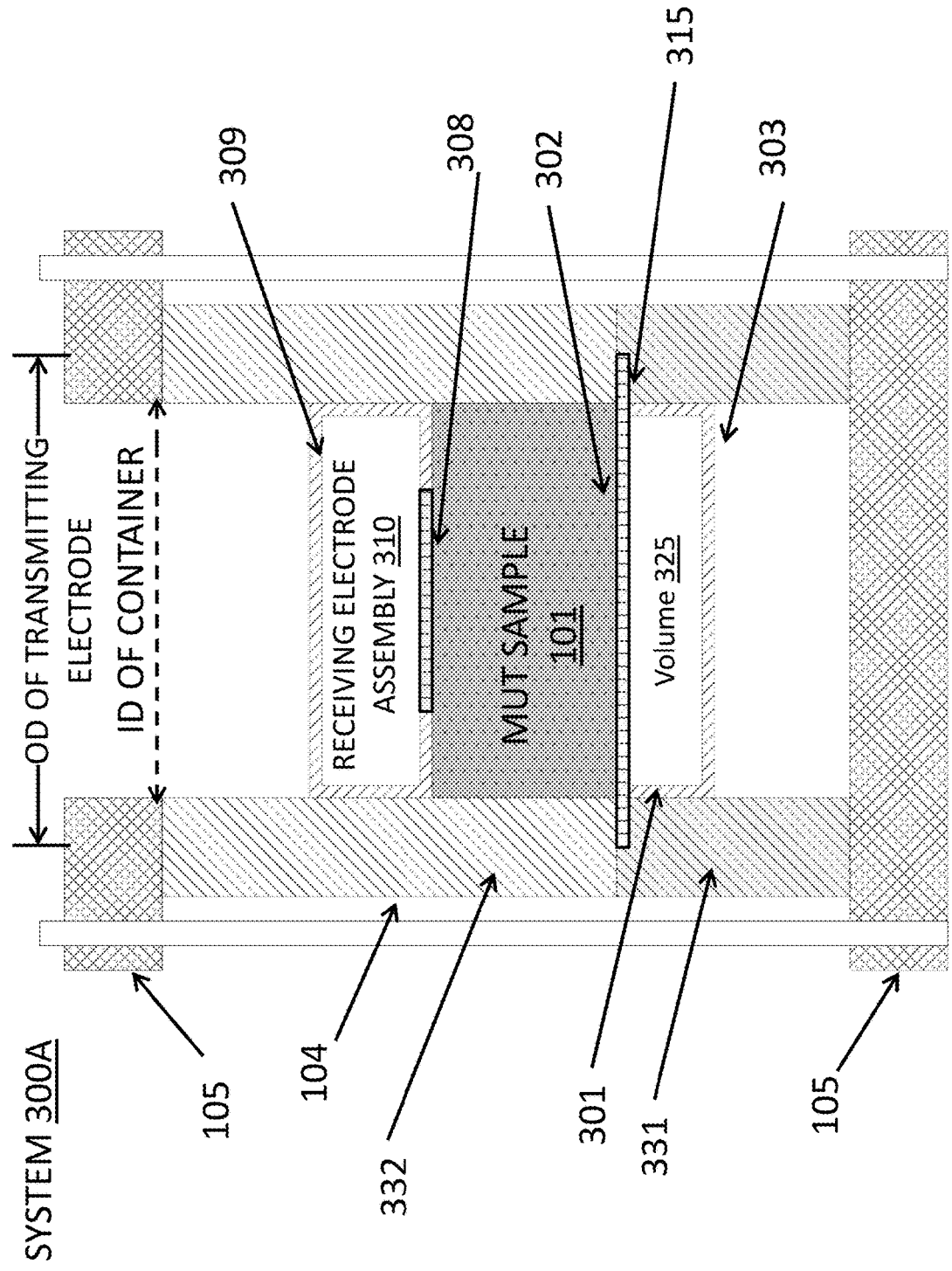
FIG. 4 shows an additional system according to various embodiments of the disclosure.

FIG. 4 presents a system 300A, depicting an alternate approach for the placement of a transmitting electrode assembly, depicted as transmitting electrode assembly 301. As shown, the transmitting electrode 302 extends beyond the inner diameter (ID) of the container. In this embodiment, the container 104 includes at least two distinct sections 331 and 332. As noted herein, the transmitting electrode 302 has a diameter larger than an inner diameter (ID) of the container 104. In some cases, one of the sections 331 of the container 104 includes a seat 315 for supporting an overhang portion of the transmitting electrode 302. In system 300A in FIG. 4, the supporting section is shown as 331. The conductive backer ground plate 303 extends from the rear face of the transmitting electrode 302 and partially surrounds the transmitting electrode 302, enclosing a volume 325 proximate to the transmitting electrode 302. The diameter of the conductive backer ground plate 303 is sized to fit the internal diameter of the cylindrical container 104 (e.g., within the ID of both sections 331 and 332). In the system 300A, the supporting member 119 (FIGS. 1, 3, 5, and 7) may not be required to support the transmitting electrode 302 and adjoining backer ground plate 303. System 300A can be operated in a similar manner as other systems described herein.

Figure 5:
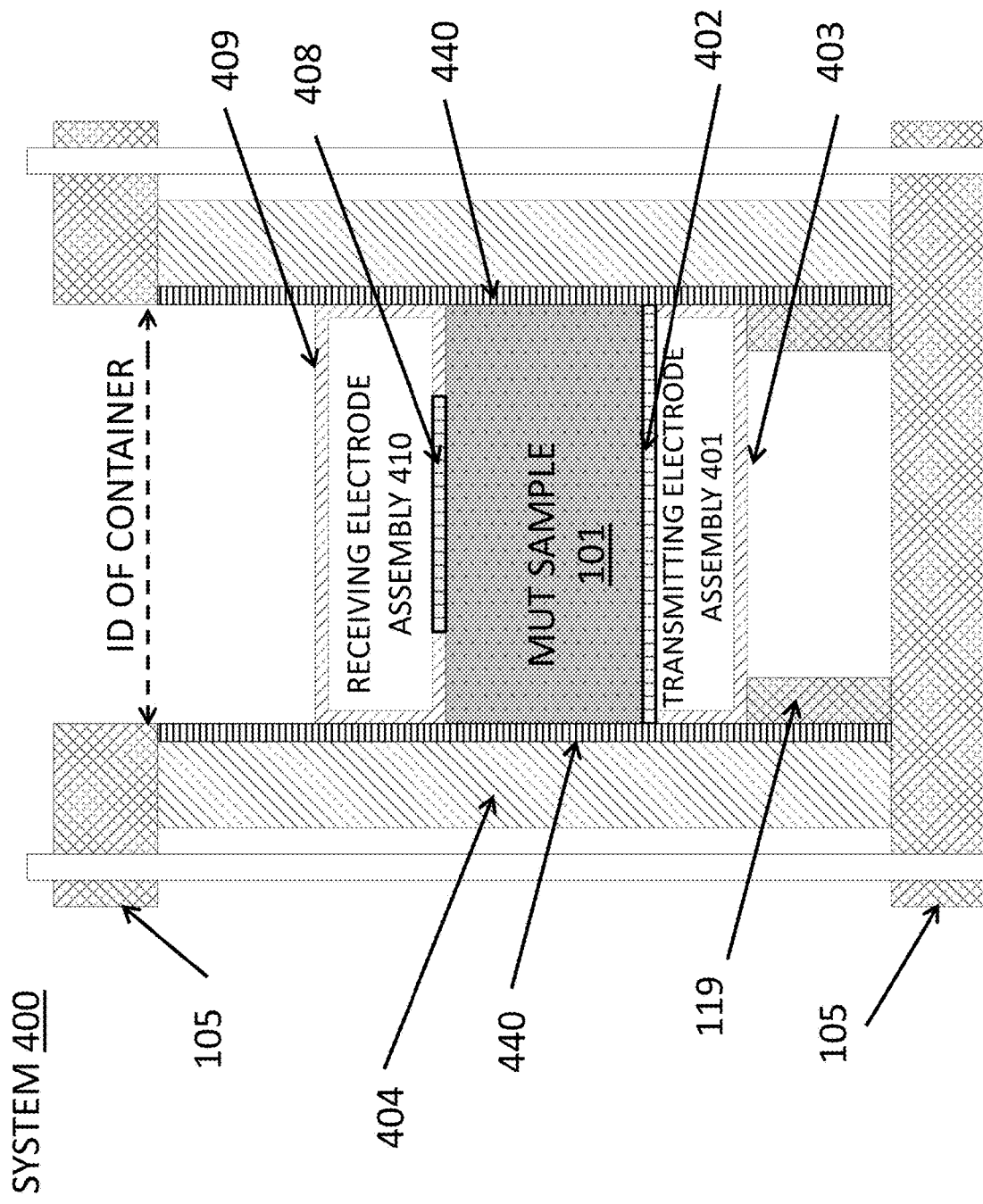
FIG. 5 shows another system according to various embodiments of the disclosure.

FIG. 5 presents an additional configuration of a system 400, for material characterization, similar to system 300 in FIG. 3. In system 400, as compared with the container 104 in FIG. 3, the container is formed of two components, a conducting structural member 404 and an electrically non-conductive liner 440. Conductive portions of the system 400 (as well as conductive portions of other systems noted herein) may be formed of conventional conductive materials such as metals, e.g., steel and aluminum. The non-conducting portions of the system 400 (as well as non-conducting portions of other systems noted herein) can be formed of materials such as plastics (e.g., polyester, polyethylene, polyvinyl chloride (PVC), polytetrafluoroethylene (Teflon), poly carbonate, and/or various fiber glass reinforce epoxy laminate materials (e.g. FR-4), and in some cases, can be formed of a poly methyl methacrylate (PMMA or acrylic), which is substantially transparent and allows for visual observation of the testing process. The liner 440 can be located radially inboard of the conducting structural member 404, and may be adhered, fastened, integrally formed, or otherwise coupled with the conducting structural member 404.

Figure 6:
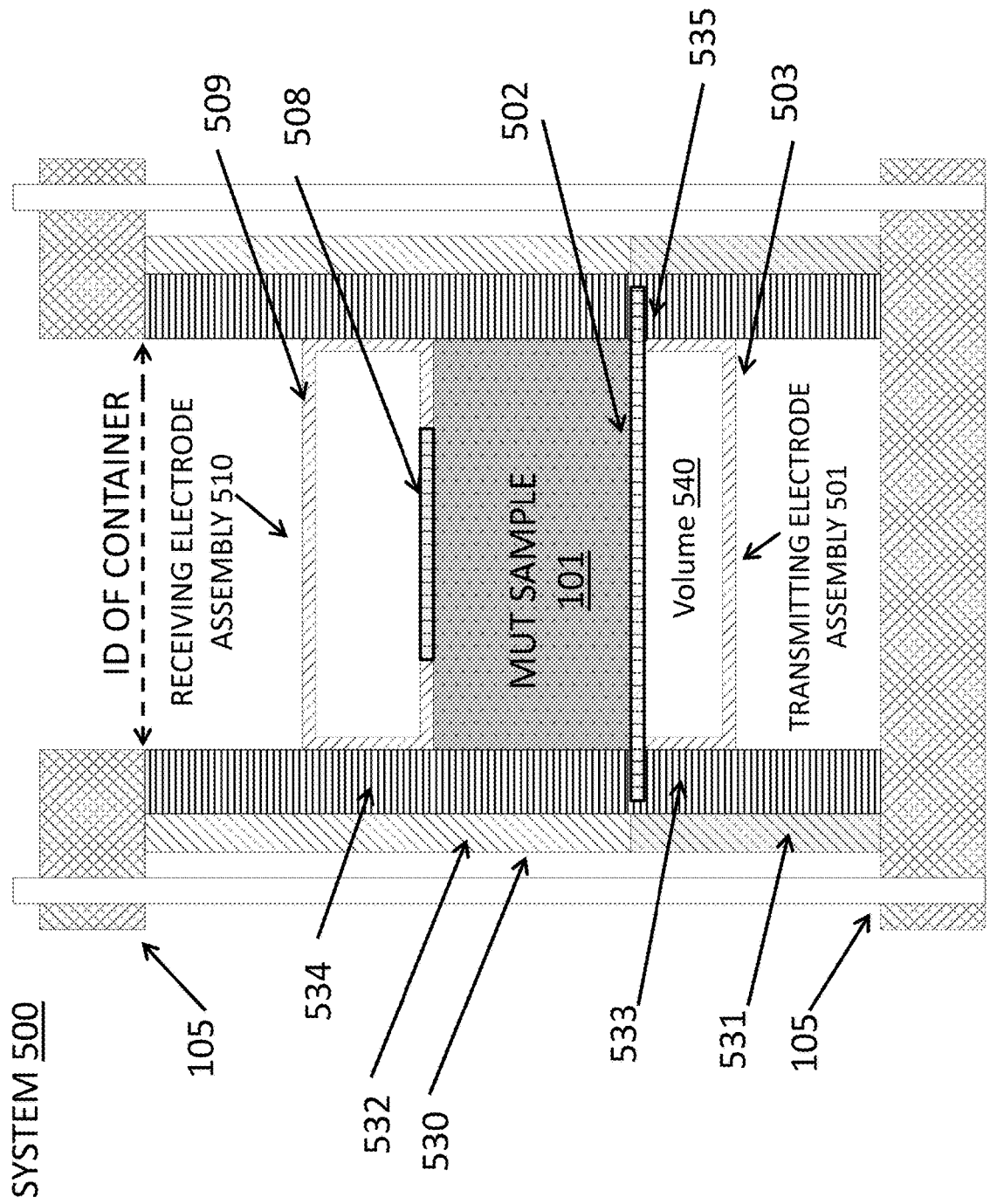
FIG. 6 shows a system according to various additional embodiments of the disclosure.

FIG. 6 presents an alternate configuration, shown as system 500, for the cylindrical container 104 in FIG. 4. In this case, system 500 shows a container 530 formed of four components 531-534. These include two conducting structural members 531 and 532, and two electrically non-conducting members 533 and 534. The conductive components may be formed of conductive materials described herein, while the non-conducting liner may be formed of non-conducting materials described herein. In some particular implementations, the container 530 is cylindrical. Similarly to the system 300 in FIG. 4, the transmitting electrode 502 in system 500 extends beyond the inner diameter (ID) of the container 530. In various implementations, the lower liner 533 includes a seat 535 for supporting an overhang portion of the transmitting electrode 502. The conductive backer ground plate 503 extends from the rear face of the transmitting electrode 502 and partially surrounds the transmitting electrode 502, enclosing a volume 540 proximate to the transmitting electrode 502. The diameter of the conductive backer ground plate 503 is sized to fit the internal diameter of the lower liner 533 (which has the same inner diameter as the upper liner 534). As compared with other implementations herein, the supporting member 119 (FIGS. 1, 3, 5, and 7) may not be required to support the transmitting electrode 502 and adjoining backer ground plate 503 in the system 500 of FIG. 6.

Figure 7:
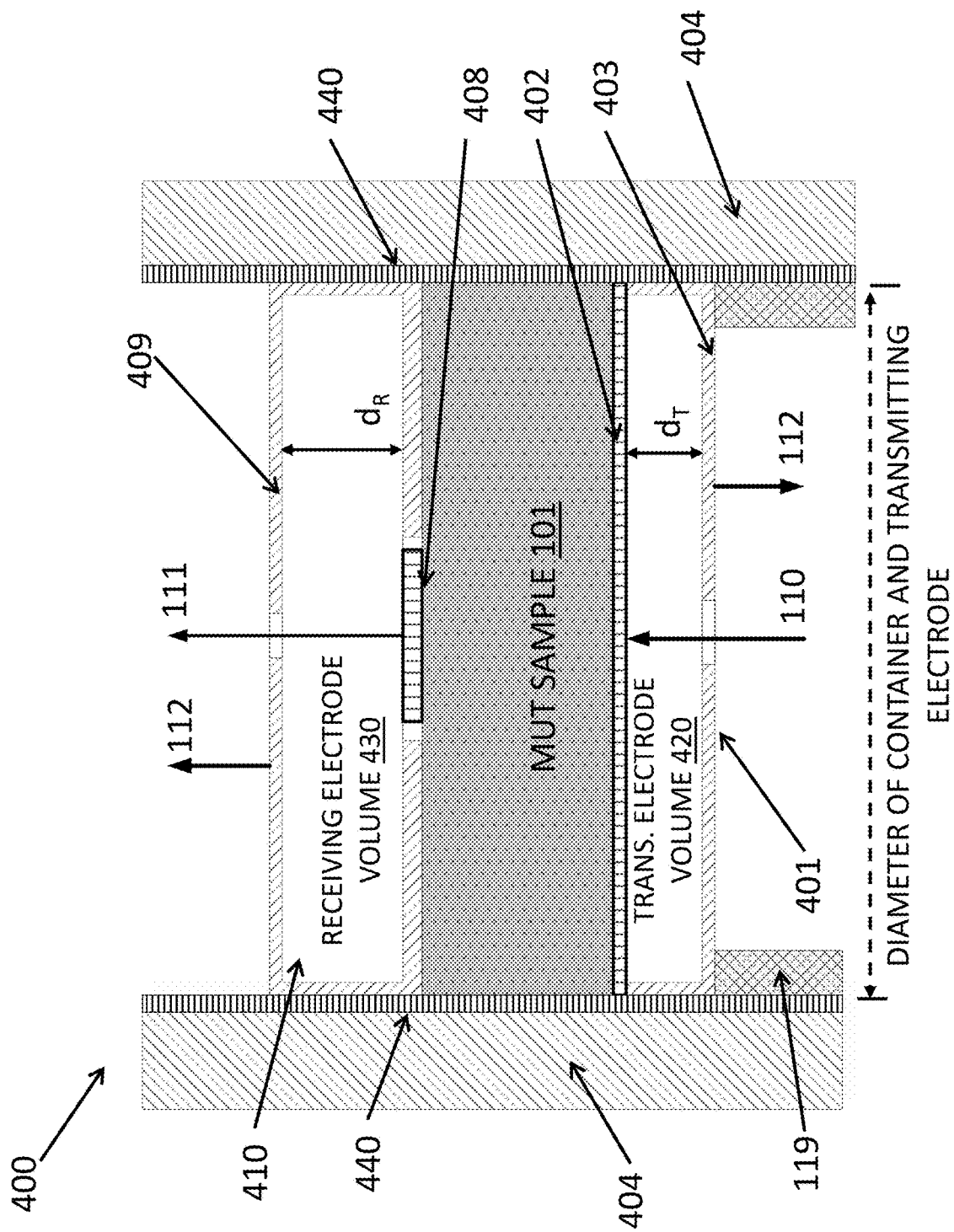
FIG. 7 shows a close-up cross-sectional view of the system of FIG. 5.
Figure 8:
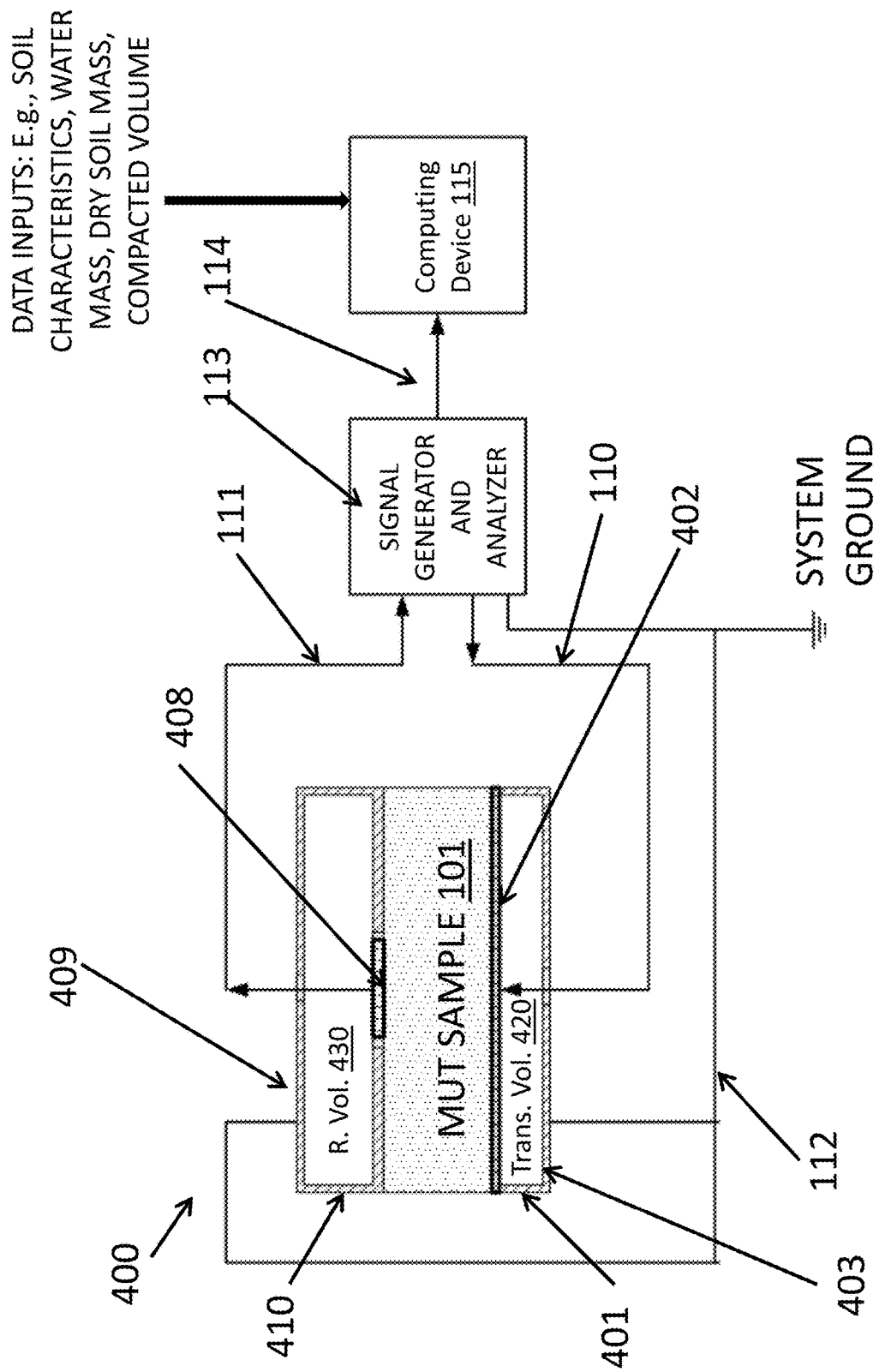
FIG. 8 is a data flow diagram illustrating connections in a system including a signal generator/analyzer, according to various embodiments of the disclosure.

FIG. 7 shows an enlarged view of system 400 (FIG. 5), including additional detailed illustration of the electrode assemblies 401, 410 and electrical connections with a signal generator and analyzer (not shown). An example signal generator and analyzer 113 is illustrated, with the electrical connections between the electrode assemblies and the signal generator/analyzer shown in the data flow diagram in FIG. 8. Returning to FIG. 7, a lead 110 from a signal generator/analyzer is shown connected with the transmitting electrode 402. An additional lead 111 is shown connecting the receiving electrode 408 with the signal analyzer/generator. Lead 110 is used to initiate transmittal of a signal from the transmitting electrode 402, through the MUT 101, and lead 111 is used to return the received signal (received at the receiving electrode 408) to the signal generator/analyzer after passing through the MUT 101. Additional leads 112 are shown connecting each of the conductive backer ground plates 403, 409 to the system ground (FIG. 8). In various embodiments, the (transmitting) diameter of the transmitting electrode 402 is larger than the (receiving) diameter of receiving electrode 408. In some implementations, the diameter of the transmitting electrode 402 is shown as approximately equal to the interior diameter (ID) of the container. In all implementations of system 400, the (transmitting) diameter of the transmitting electrode 402 is larger than the (receiving) diameter of the receiving electrode 408 for reasons noted herein.

Referring to system 400 in FIG. 7 and the corresponding data flow in FIG. 8, the backer ground plate 403 for the transmitting electrode 402 and the backer ground plate 409 for the receiving electrode 408 are connected to a system ground from the signal generator/analyzer 113. In various embodiments, it is beneficial that the electric potential of the backer ground plates 403 and 409 be equal. The parasitic capacitance of the volume created between the respective backer ground plates and electrodes (volumes 420 and 430) are affected by the potential of both the backer ground plate and the corresponding transmitting and receiving electrodes. By controlling the electric potential of the two backer ground plates such that those potentials are identical, the design values for the parasitic capacitances can be more easily defined and maintained. In certain implementations, the transmitting electrode backer ground plate 403 can have a diameter approximately equal to the ID of the (e.g., cylindrical) container 404 with the (e.g., non-conducting) liner 440. The transmitting electrode backer ground plate 403 at least partially encloses a volume 420 behind the electrode 402. The receiving electrode backer ground plate 409 has a surface that is coplanar with the surface of receiving electrode 408 and at least partially encloses a volume 430 behind the receiving electrode 408. Both backer ground plates 403 and 409 are electrically insulated from their respective electrodes 402 and 408 by an air gap of distance $d_T$ for the transmitting electrode assembly 401 and of distance $d_R$ for the receiving electrode assembly 410.

The conductive backer ground plates 403, 409 around the transmitting electrode 402 and the receiving electrode 408 can help to control the parasitic capacitances generated by the electric field lines which traverse between the electrodes 402, 408. These backer ground plates 403, 409 can be used to control the electric field lines between the electrodes 402, 408 as they pass through the MUT sample 101. As the transmitted electromagnetic signal is scanned over a range of frequencies, the amplitude of the electric potential of the signal remains approximately constant and controls the potential of the ground plate. The enclosed volume 420 created by the backer ground plate 403 at least partially surrounding the transmitting electrode 402 helps to mitigate the parasitic capacitance (e.g., by designing the enclosed volume 420 and the distance $d_T$ based upon a computation of the system impedance using a computational tool such as Comsol's Multiphysics) between the backer ground plate 403 and the transmitting electrode 402, and is controlled to limit the effects of the parasitic capacitance on the impedance measurements. The volumes 420 and 430 are determined by the distances $d_T$ and $d_R$ and the diameter of the electrodes 402 and 408 ($D_{TX}$ and $D_{RX}$). The optimization attempts to balance the current drive requirements of the transmit circuit, the parasitic inductances of the wiring, signal strength, and immunity with respect to noise and inductive/capacitive coupling. This results in a system specific solution. An example range of the ratios of $d_R/D_{RX}$ and $d_T/D_{TX}$ are from 1:1000 to 1:1.

The receiving electrode 408 and its corresponding backer ground plate 409 act in a different manner. The signal arriving at the receiving electrode 408 after passing through the MUT sample 101 varies with the material type (e.g., soil type, water content, compaction level, and frequency). As the transmitted signal from electrode 402 passes through the MUT sample 101, the strength of the signal (magnitude) is attenuated, and the phase relation is changed. As such, the potential of the signal and its phase relative to the transmitted signal is quite variable (by material type), and unknown a priori. The parasitic capacitance due to the field between the receiving electrode 408 and its backer ground plate 409 has a larger effect on the measurement (when compared with the transmitting electrode 402 and its backer ground plate 403) due to the attenuation of the transmitted signal at the receiving electrode 408. Therefore, the ability to reduce and control the parasitic capacitance for the receiving electrode 408 is significant to the quality of the data measured. Again, this is achieved by the combination of controlling the potential of the backer ground plate 409 and by designing the volume 430 enclosed by the receiving electrode 408 and the conductive backer ground plate 409 based upon a computation of the system impedance, e.g., by use of a computational tool such as Comsol's Multiphysics.

FIG. 8 is a schematic data flow diagram illustrating connections between the electrodes 402, 408, the signal generator/analyzer 113 and a computing device 115 configured to determine characteristics of the MUT sample 101. The computing device 115 can include any conventional computing architecture capable of performing processes as described herein and can be programmed to perform particular functions. The computing device 115 can include one or more processors and a memory, which may store program code and/or program logic for performing various functions according to embodiments. As noted herein, the system ground 112 of the signal generator/analyzer 113 is connected to the transmitting conductive backer ground plate 403 and the receiving conductive backer ground plate 409.

The electrical connections illustrated in FIG. 8 can be applicable to systems 200, 300, 300A, 400, and 500, although they are shown in this example as connections made with system 400.

As noted herein, the signal generator/analyzer 113 may include conventional commercial instruments such as a Keysight network analyzer or impedance analyzer, or circuits such as those described in U.S. Pat. No. 7,219,024 or U.S. Patent Application No. 62/434,789 (each of which is incorporated by reference in its entirety). The transmitting (or high) side 110 of the signal generator/analyzer 113 is connected to the transmitting electrode (e.g., transmitting electrode 102 in FIG. 3, or transmitting electrode 402 in FIG. 7). The receiving (or low) side 111 of the generator/analyzer 113 is connected to the receiving electrode (e.g., receiving electrode 108 in FIG. 3, or receiving electrode 408 in FIG. 7). Both the transmitting backer ground plate (e.g., transmitting backer ground plate 103 in FIG. 3, or transmitting backer ground plate 403 in FIG. 7) and the receiving backer ground plate (e.g., receiving backer ground plate 109 in FIG. 3, or receiving backer ground plate 409 in FIG. 7) are connected to the ground 112 of the signal generator/analyzer 113. The signal generator/analyzer 113 is also configured to analyze the signal at each frequency in the range of frequencies used. The signal that is transmitted through the MUT sample 101 is attenuated and the phase shifted during the transmission. The analyzer function of the signal generator/analyzer 113 records the change in signal magnitude and phase between the transmitted and received signal for each test frequency. These data are transmitted as signal comparison data 114 to the computing device 115. The measured impedance of MUT sample 101 is computed for each frequency in the range of test frequencies (e.g., the range of frequencies for soil testing is from 100 kHz to 100 MHz) and correlated with the other test data (e.g., soil characteristics, water mass, dry soil mass and compacted volume) to develop the algorithm for the correlation of the measure impedance characteristics to soil dry density and gravimetric moisture level.

Figure 9:
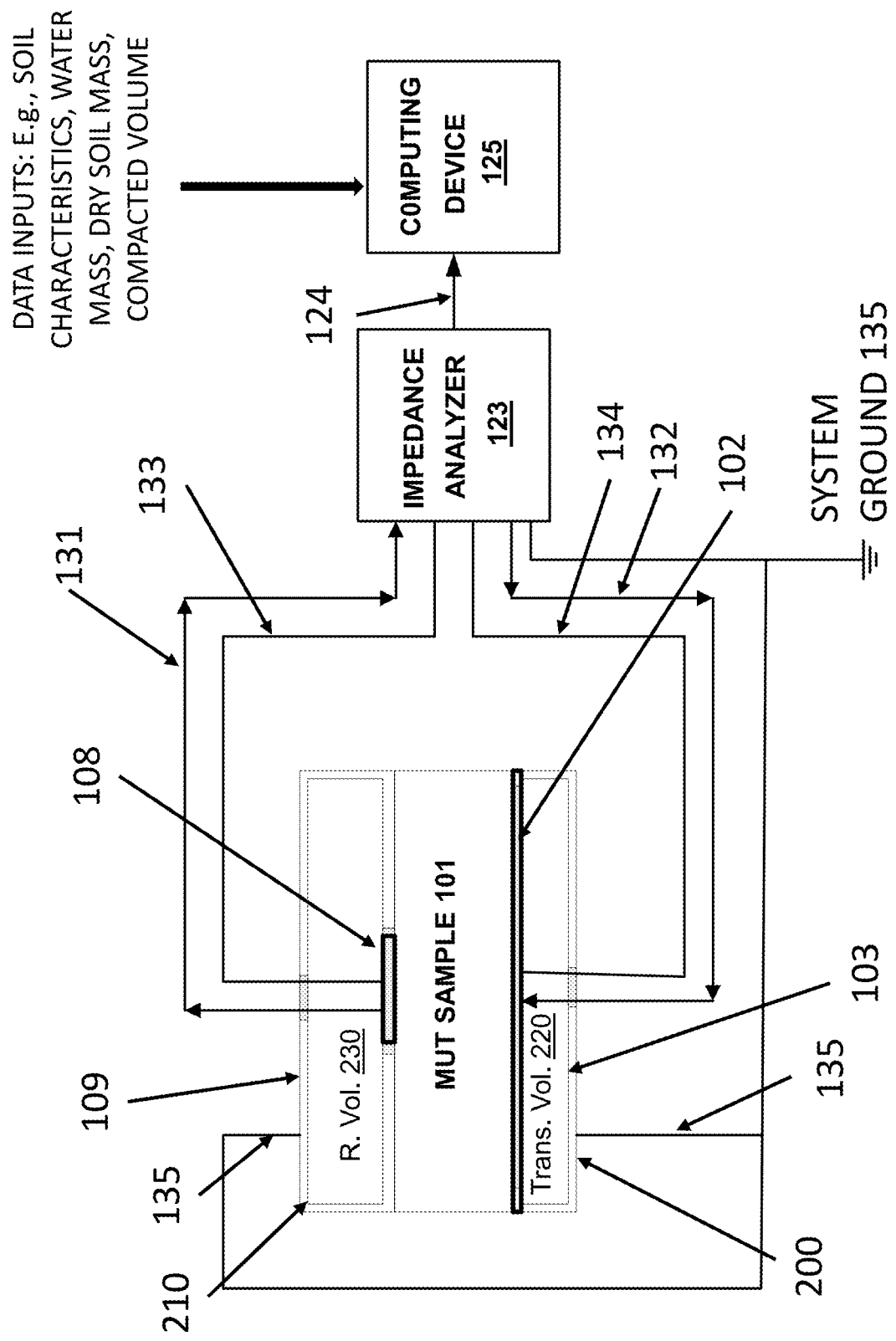
FIG. 9 is an additional data flow diagram illustrating connections in a system including a signal generator/analyzer, according to various embodiments of the disclosure.

FIG. 9 is a schematic data flow diagram illustrating connections between electrodes (e.g., electrodes 102, 108), an impedance analyzer 123 (e.g., the Keysight E4990) with four terminal connections, and a computing device 125 configured to determine physical characteristics of the MUT sample 101. In this embodiment, there are two terminal connections on the impedance analyzer 123, which transmits a current signal (over conductor 132) over a range of frequencies to the transmitting electrode (e.g., transmitting electrode 102). This signal passes through the MUT 101 to the receiving electrode (e.g., receiving electrode 108) and is transmitted back to the analyzer 123 via a conductor 131. The voltage of the transmitting electrode (e.g., transmitting electrode 102) is measured by the analyzer 123 using conductor 134. The voltage of the receiving electrode (e.g., receiving electrode 108) is measured by the analyzer using the conductor 133. The analyzer 123 generates a value of an impedance characteristic over the range of frequencies of the transmitted signal. This impedance value for each specific frequency is transmitted (as data shown by 124) to the computing device 125. The computing device 125 is configured to determine characteristics of the MUT sample 101 based upon these impedance values. The computing device 125 can include any conventional computing architecture capable of performing processes as described herein and can be programmed to perform particular functions. The computing device 125 can include one or more processors and a memory, which may store program code and/or program logic for performing various functions according to embodiments. The system ground 135 of the impedance/analyzer 123 is connected to the transmitting conductive backer ground plate (e.g., transmitting conductive backer ground plate 103) and the receiving conductive backer ground plate (e.g., receiving conductive backer ground plate 109). The electrical connections illustrated in FIG. 9 can be similarly applied to systems 200, 300, 300A, 400, 500 and 900.

The correlation between an impedance characteristic and a physical characteristic may be developed with any number of well-known correlation methods such as analysis of variations (ANOVA), neural networks, multiple regressions, and deep learning. A determination as to which correlation process, which impedance characteristic(s), and which frequency range may result in the best correlation would be decided based upon the mix of variables that provides the most statistically significant results.

The test data can be gathered using standard ASTM tests such as D4818, D422, D698, and D1557. Additional physical properties that may be included in the data for the algorithm development are the mass of water added to the dried soil, the mass of the dried soil, and the compaction volume (compressed sample height).

Figure 10:
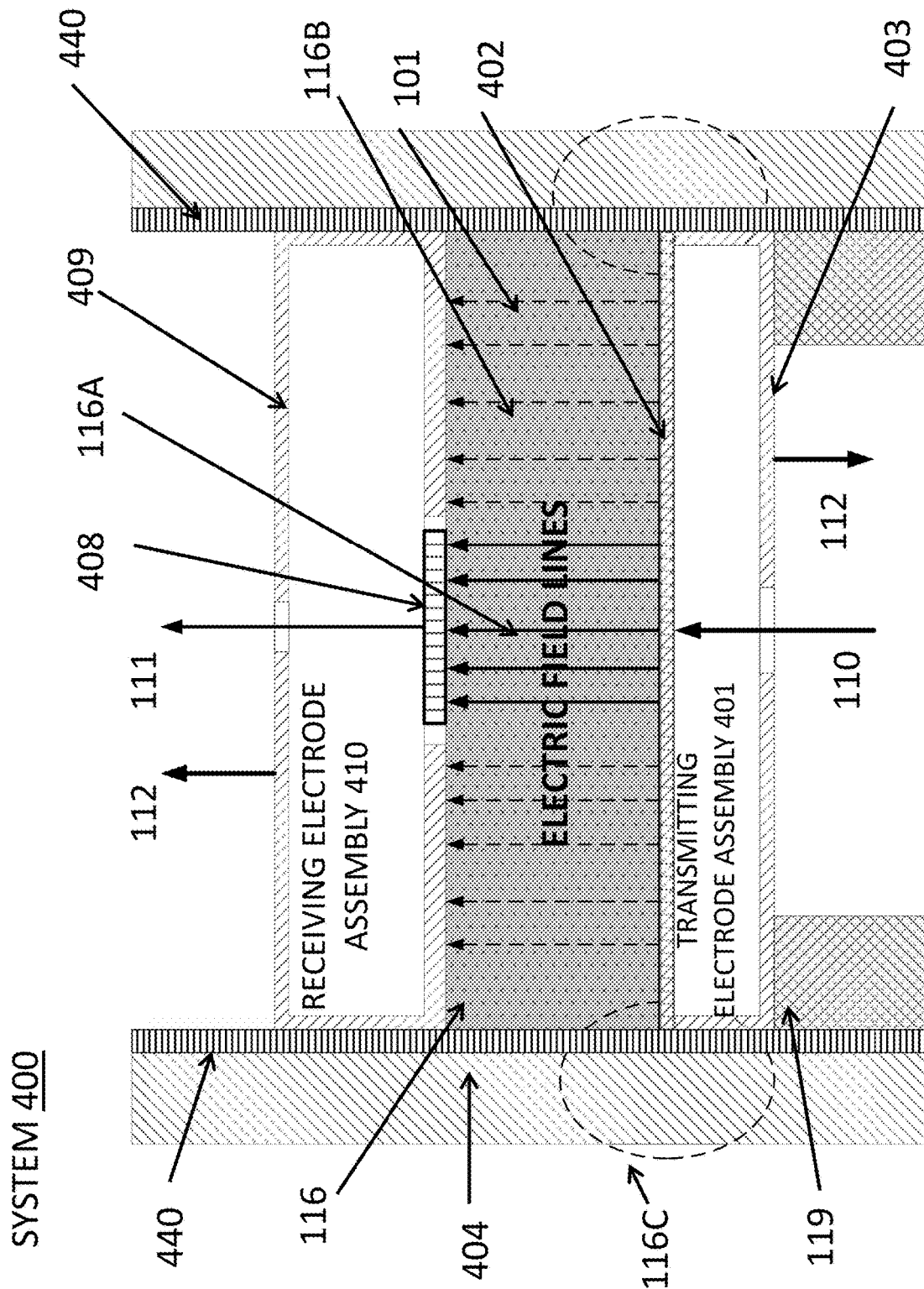
FIG. 10 shows electric field lines during a testing operation with the system of FIG. 5.

FIG. 10 is a schematic cross-sectional depiction of system 400, illustrating electric field lines 116 relative to the respective backer ground plates 403, 409. A first subset 116A of the electric field lines 116 are shown as traveling perpendicularly (relative to transmitting/receiving surfaces) directly from the transmitting electrode 402 to the receiving electrode 408. As the transmitting electrode 402 has a larger area (e.g., diameter in the case of a circular electrode, or surface area in the case of another shape) than the receiving electrode 408, and the receiving backer ground plate 409 is in the same plane as the receiving electrode 408 (and surrounds the receiving electrode), an additional subset 116B of the electric field lines 116 are shown travelling perpendicularly from the transmitting electrode 402 to the receiving electrode backer ground plate 409. In this configuration, the receiving electrode backer ground plate 409 acts as a guard to the field lines 116A traversing between the transmitting electrode 402 and the receiving electrode 408 and ensures that the field lines 116A going directly from the transmitting electrode 402 to the receiving electrode 408 are perpendicular to the electrode surfaces. An additional subset 116C of field lines 116 from the transmitting electrode 402 are transmitted to the transmitting conductive backer ground plate 403 and pass through the MUT sample 101. These field lines 116C affect the parasitic capacitance load on the transmitting electrode 402, but do not affect the field lines 116A that produce the measurement data.

Figure 11:
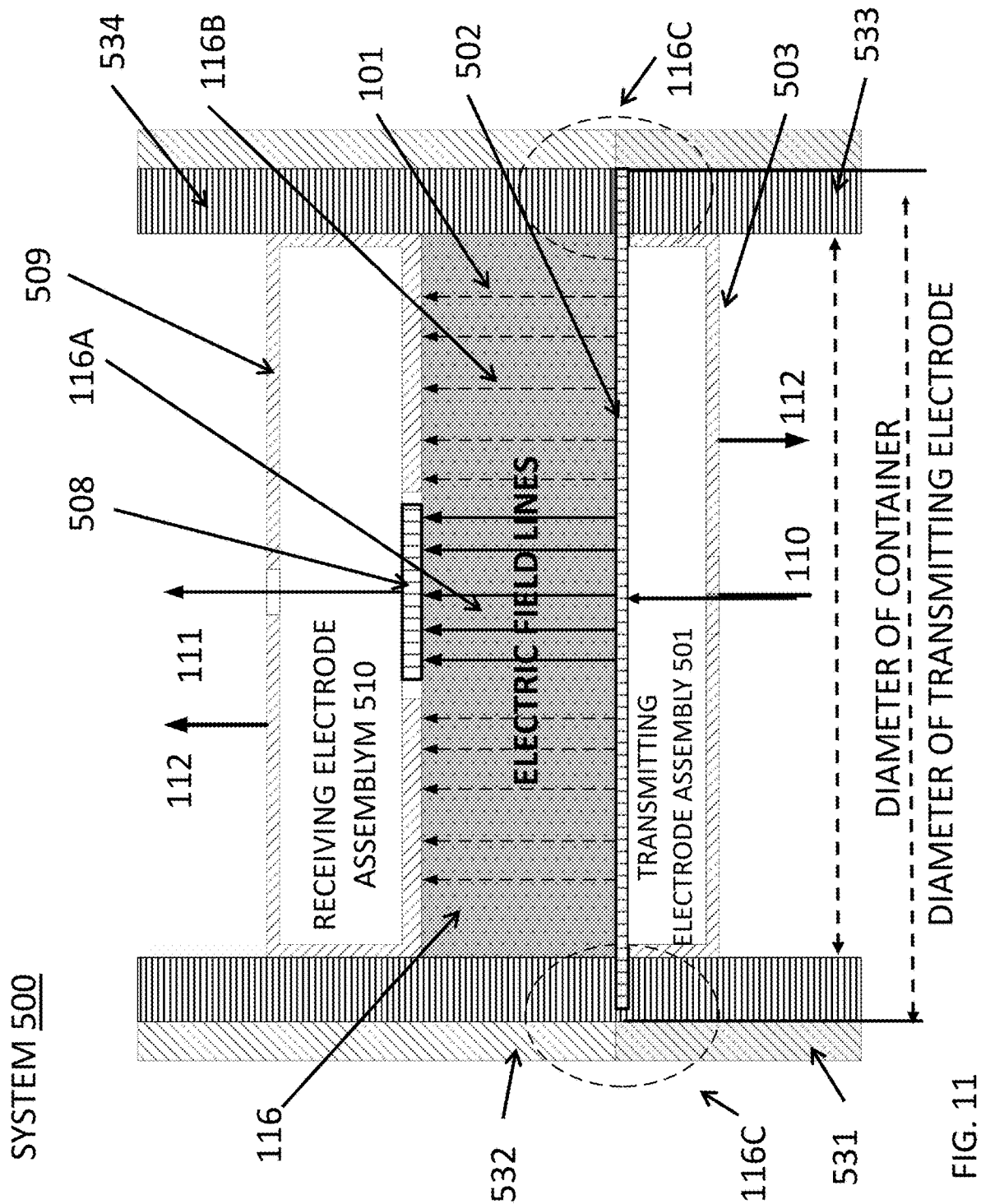
FIG. 11 shows electric field lines during a testing operation with the system of FIG. 6.

An additional view of system 500 is shown in an enlarged cross-sectional depiction in FIG. 11, which additionally illustrates electromagnetic field lines. As in the depiction of system 500 in FIG. 6, the transmitting electrode 502 has a transmitting area (e.g., diameter in the case of a circular electrode) that is greater than the ID of the container (including the outer segments 531 and 532 and the liner segments 533 and 534). In these implementations, the lower liner 533 (or upper liner 534) can include a seat for supporting an overhang portion of the transmitting electrode 502 extending beyond the ID of the non-liner of the container. The interactions of the field lines 116 are similar to those described with reference to system 400 in FIG. 10. In system 500, the supporting member 119 (FIGS. 1, 3, 5, and 7) may not be required to support the transmitting electrode 502 and adjoining backer ground plate 503. This embodiment is a simple mechanical change and does not affect any of the electrical performance previously described.

The impedance of materials, for example, soils, is a complex quantity made up of contributions of the resistance and capacitance of the soil when an oscillating electromagnetic signal is passed through it. The equation for this is $$Z = Z_R + Z_C$$

where Z is the total impedance, $Z_R$ is the impedance component due to the resistance, and $Z_C$ is the impedance component due to the capacitance. For the range of frequencies used for soil testing, the inductive effects of the soil are negligible. $Z_R$ and $Z_C$ are given by the following relations:

$$Z_R = R$$

$$Z_C = \frac{1}{i\omega C}$$

where R is the resistance and C is the capacitance. The capacitance C is given the following relation:

$$C = \varepsilon_r \varepsilon_0 [A_R / H_{sample}]$$

where $\varepsilon_r$ is the relative permittivity of the soil (also called the dielectric), co is a constant permittivity of free space, $A_R$ is the area of the receiving electrode (e.g. receiving electrodes 108, 308, 408, or 508), and $H_{sample}$ is the height of the sample and also the distance between the electrodes. The values of Z, $Z_R$, and $Z_C$ are all functions of the properties of the soil, the compaction level (density) of the soil, the moisture level of the soil, and the frequency of the electromagnetic signal.

Figure 12:
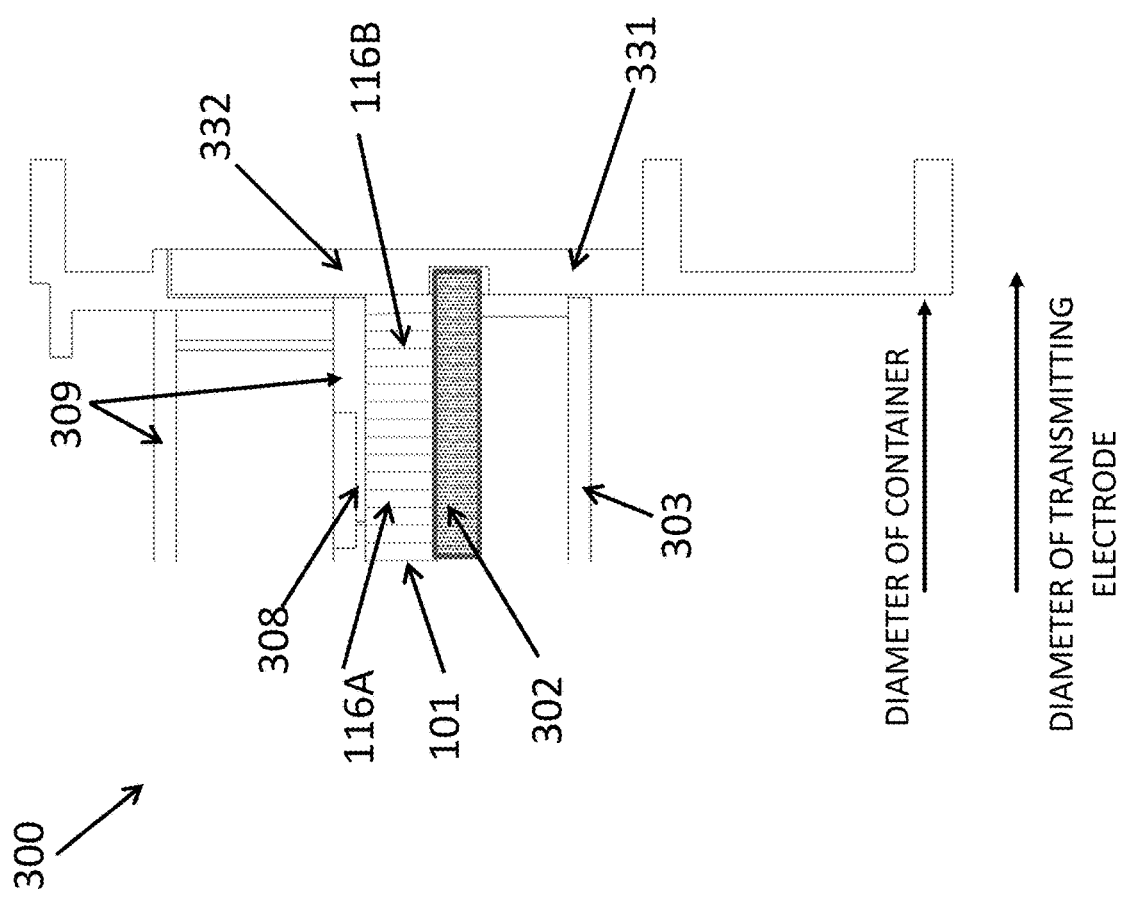
FIG. 12 shows a cross-sectional view of computed field lines associated with the system of FIG. 6.

FIG. 12 illustrates examples of field lines 116A and 116B modeled using Comsol Multiphysics for system 300A in FIG. 4. In this example, the MUT sample 101 (e.g., soil) has a height of 20 mm (about three quarters of an inch) and an s, (dielectric) value of 10. A dielectric value of 10 is typical of a soil with a low moisture level. Soil solids have a dielectric value of about 7. Water has a dielectric value of about 80. In this embodiment, upper section 332 and lower section 331 of the cylinder are constructed out of poly methyl methacrylate (PMMA or acrylic) to allow for visual observation of the testing process. Upper section 332 and/or lower section 331 can also be formed of other non-conducting materials such as conventional plastics or glass, such as plastics like polyester, polyethylene, polyvinyl chloride (PVC), polytetrafluoroethylene (Teflon), poly carbonate, and composites like various fiber glass reinforce epoxy laminate materials (e.g. FR-4). As can be seen, the electric field lines 116A between the transmitting electrode 302 and receiving electrode 308 are perpendicular to the electrodes with no non-linear deviations. These field lines 116A produce the impedance characteristic data for the MUT sample 101. The electric field lines 116B between the transmitting electrode 302 and the receiving backer ground plate 309 and are also perpendicular to the ground plates 303, 309 and the transmitting electrode 302 with no non-linear deviations.

Figure 13:
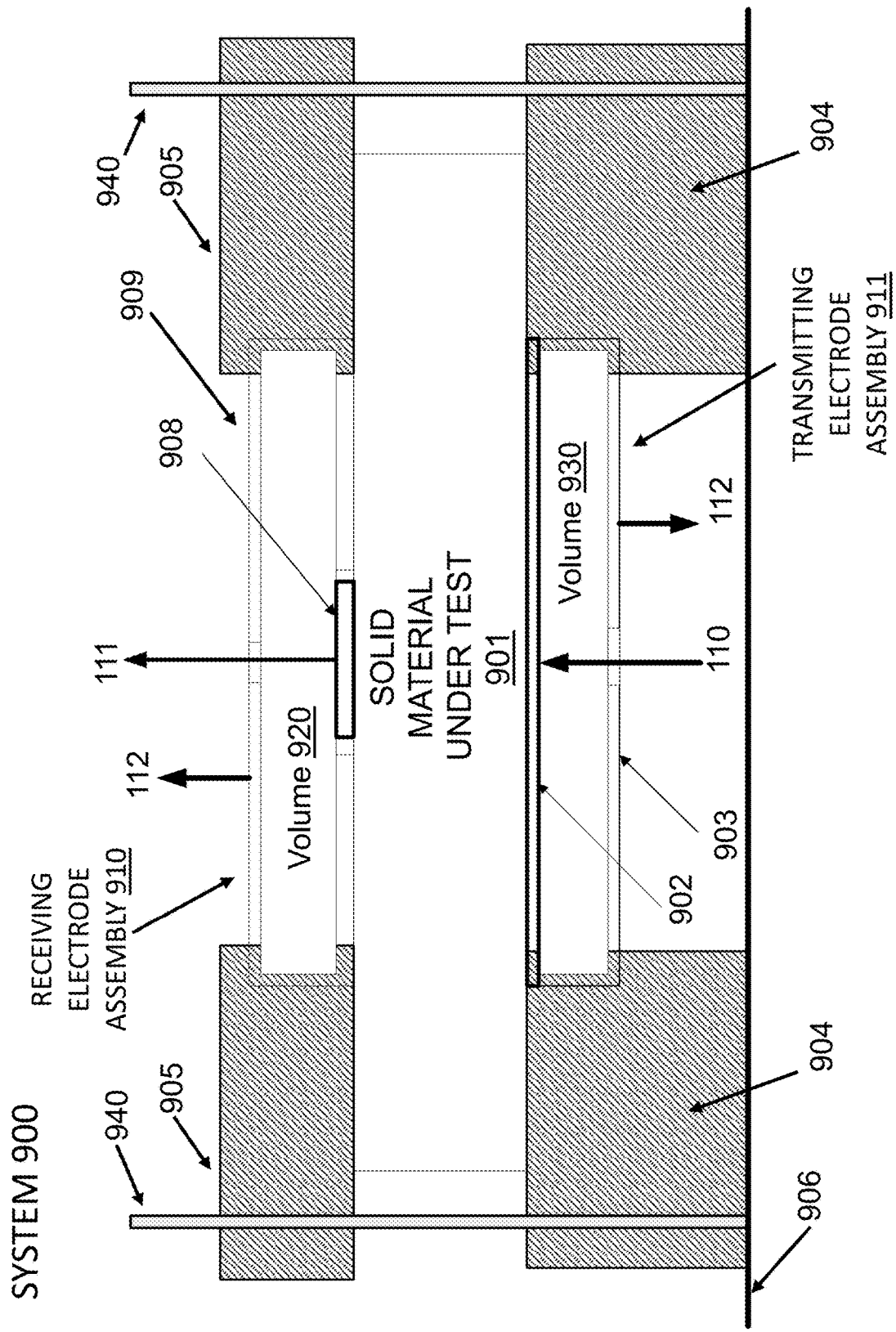
FIG. 13 shows a cross-sectional view of a system according to an additional embodiment for testing a solid material under test without an enclosing electrically non-conducting container.

FIG. 13 illustrates a system 900 according to various additional embodiments. In these embodiments, system 900 is configured for use in determining impedance characteristics of a solid MUT 901 without the MUT 901 being placed in an electrically non-conducting container (e.g., container 104, FIG. 3). In some cases, the solid MUT 901 includes a concrete or asphalt sample, such as a cured concrete cylinder or asphalt core.

Referring to FIG. 13, the solid MUT 901 is placed directly on a transmitting electrode assembly 911, which is supported by electrically non-conducting support(s) 904, which are in turn supported on an underlying structure 906 such as a floor, tabletop, or platform. A receiving electrode assembly 910 is placed on top of the solid MUT 901. Additional electrically non-conducting support(s) 905 can be placed on top of the solid MUT 901 and provide mechanical support for the receiving electrode assembly 910 (e.g., such that the non-conducting supports 904 and 905 include slots or ledges for supporting the corresponding electrode assemblies 910, 911). In various embodiments, the electrode assemblies 910 and 911 are positioned such that the center of each of the transmitting electrode 902 and the receiving electrode 908 are aligned. In some particular embodiments, the non-conducting supports 904 and 905 are separate components, however, in some cases, one or more non-conducting lower supports 904 can be coupled with (or substantially unitary with) one or more non-conducting upper supports 905. In various particular embodiments, the solid MUT 901 has a greater width (or diameter, depending upon its shape) than the outer dimension of the backer ground plates 903, 909, such that a portion of the solid MUT 901 extends outside of the outer dimension of the electrode assemblies 910, 911. In some cases, lower support 904 can include a slot or shelf for supporting the transmitting electrode assembly 911. Additionally, or alternatively, in some embodiments, the upper support 905 can also include a slot or shelf for supporting the receiving electrode assembly 910. In some cases, as shown in FIG. 13, the supports 904 and 905 may extend radially beyond the MUT 901 and be aligned by use of guide rods 940.

As noted herein, the capacitive volumes 920 and 930 enclosed by the electrode assemblies 910 and 911 are controllable to optimize the parasitic capacitances resulting from the effects of the electromagnetic field lines which emanate from both the transmitting electrode 902 and the receiving electrode 908, and go to the backer ground plates 903 and 909, and the field lines that pass through the MUT 901 and go to the receiving backer ground plate 909.

Figure 14:
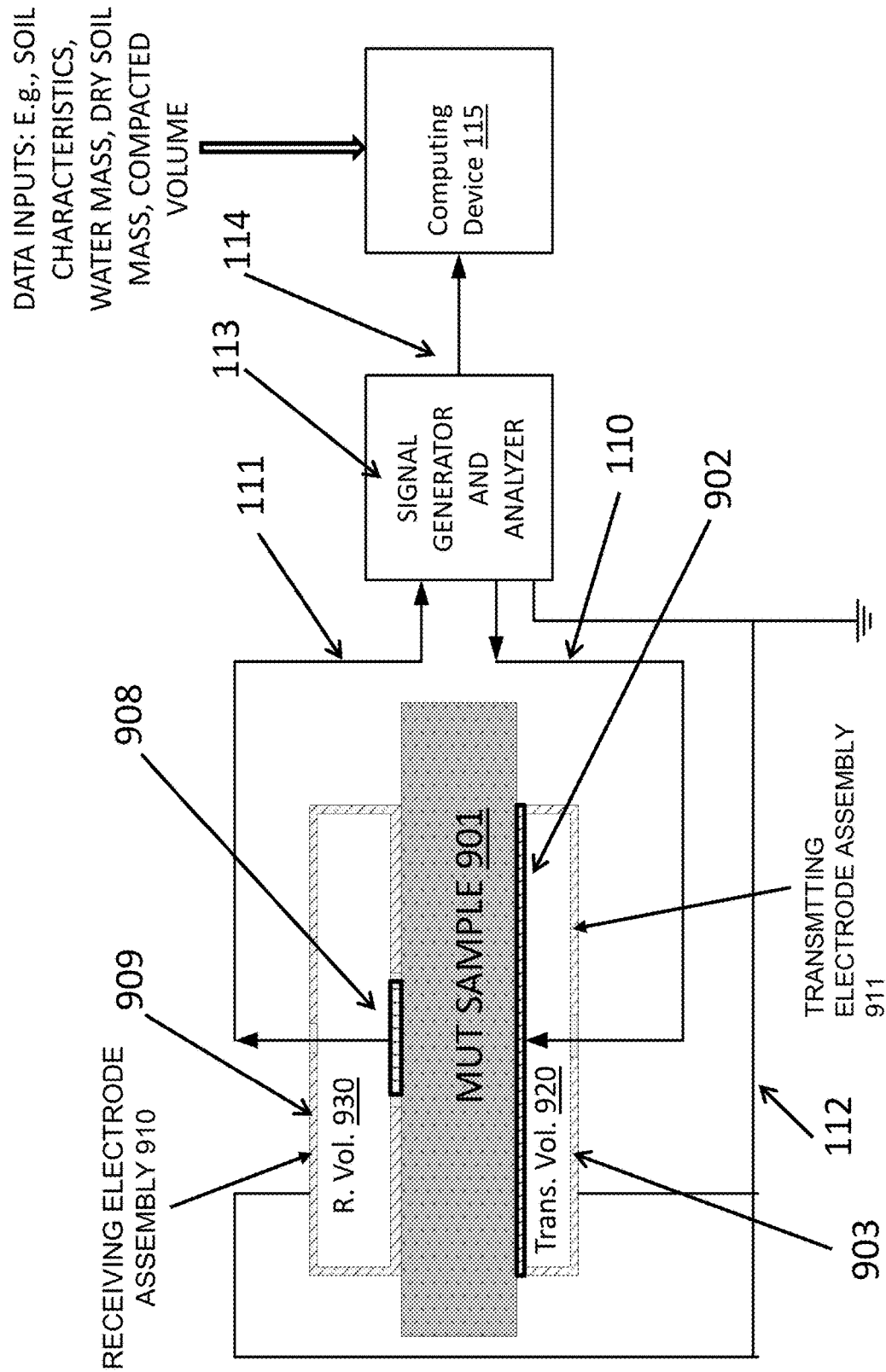
FIG. 14 is an additional data flow diagram illustrating connections in the system of FIG. 13, including connections with a signal generator/analyzer, according to various embodiments of the disclosure.

FIG. 14 illustrates electrical circuit connections in system 900 (FIG. 13). As shown, these electrical circuit connections may resemble those in the circuit diagram of system 200 depicted in FIG. 8. As shown in FIG. 14, however, the solid MUT 901 may extend outside of the outer dimension of the electrode assemblies 910 and 911.

It is understood that while various embodiments illustrate and describe transmitting electrodes (e.g. 102, 302, 402, 502 and 902) and respective receiving electrodes (e.g. 108, 308, 408, 508 and 908) as oriented in particular manners, it is understood that these orientations could be modified without modifying the teachings of the disclosure. For example, electrodes orientations can be reversed (e.g., transmitting electrodes placed above receiving electrodes), or entire orientations of systems disclosed herein can be altered (e.g., such that transmitting/receiving electrodes are aligned on the same horizontal plane, or at any angle relative to normal).

In various particular embodiments, electrodes shown and described have a circular (or nearly circular, within margins of measurement error) transmitting/receiving surface. That is, discussions of variation in the transmitting/receiving area of these electrodes necessarily relates to a variation in the diameter of these surfaces. However, as described herein, in other embodiments, the transmitting and/or receiving electrode surfaces may take other forms (e.g., elliptical, rectangular, rectangular with rounded corners).

The design of the individual electrodes in the various arrays discussed with reference to one or more FIGURES may be circular in shape. However, in some embodiments, a circular-shaped electrode may limit the potential of field concentration available if the desired area of detection in the MUT included a corner or a point. In various embodiments, at least one of the electrodes has an ellipsoid shape. In various other embodiments, as noted herein, at least one of the electrodes has a rectangular shape with rounded corners. In various embodiments, the electrodes may have a uniform area to match their signal generation capacity with corresponding receiving capacity. In some cases, the diameter of the electrodes relative to the distance between the centers of the electrodes may vary. The Applicants have further discovered that there may be a tradeoff between the electric field strength of the array, the geometry factor of the array, and the signal-to-noise ratio of the measurement obtained by the array. Applicants have further discovered that these factors are not determinant a priori to establish the optimum area of the electrode.

Various approaches described allow for determining a physical property of one or more portions (e.g., sub-voxel or a number of sub-voxels) of the MUT 101, e.g., as described in U.S. Pat. Nos. 9,465,061 and 9,804,112 (each of which is herein incorporated by reference in its entirety). In various embodiments, a number of measurements of the physical property(ies) of interest are measured by conventional means and correlated with the measured variations of the measured (and computed) complex impedance (of the MUT, including one or more voxels and sub-voxels) using the apparatuses/systems/approaches described herein. In various embodiments, the number of measurements can be sufficiently large such that the resulting correlation is statistically significant. The impedance measurements can be made with the same type of array that will be used to inspect unknown MUTs, or in other embodiments, a parallel plate electrode arrangement may be used. Regardless of the array geometry, the measurements may also be made over a range of frequencies. Further embodiments include a method of developing an algorithm to correlate the physical property to the measured impedance (of the voxel or sub-voxel over the selected range of frequencies), which may use any number of well-known correlation methods such as analysis of variations (ANOVA), neural networks, multiple regressions, and deep learning. A determination as to which process, impedance characteristic(s) and frequency range may ensure that the best fit may be made by selection of the one that provides the most statistically significant results.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random-access memory or both. Components of a computer include a processor for executing instructions and one or more memory devices for storing instructions and data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for measuring an electromagnetic impedance characteristic of a material under test (MUT), the system comprising:
    an electrically non-conducting container sized to hold the MUT, the electrically non-conducting container having a first opening at a first end thereof and a second opening at a second, opposite end thereof;
    a transmitting electrode assembly at the first end of the electrically non-conducting container, the transmitting electrode assembly having:
        a transmitting electrode with a transmitting surface; and
        a transmitting electrode backer ground plate at least partially surrounding the transmitting electrode, the transmitting electrode backer ground plate being insulated from the transmitting electrode; and
    a receiving electrode assembly at the second end of the electrically non-conducting container, the receiving electrode assembly having a receiving electrode with a receiving surface.

2. The system of claim 1, wherein the transmitting electrode backer ground plate is electrically grounded and extends from a plane formed by the transmitting electrode and creates an electrically isolated volume proximate to the transmitting electrode, wherein the transmitting electrode backer ground plate is formed of an electrically conductive material and comprises a recess corresponding with the transmitting electrode, and wherein the plane formed by the transmitting electrode is substantially parallel with a surface of the MUT.

3. The system of claim 2, wherein the receiving electrode assembly further comprises:
    a receiving electrode backer ground plate at least partially surrounding the receiving electrode, the receiving electrode backer ground plate being electrically grounded and insulated from the receiving electrode, wherein the receiving electrode backer ground plate extends from a plane formed by the receiving electrode and creates an electrically isolated volume proximate to the receiving electrode, wherein the receiving electrode backer ground plate is formed of an electrically conductive material and comprises a recess corresponding with the receiving electrode, and wherein the plane formed by the receiving electrode is substantially parallel with a surface of the MUT, wherein the receiving electrode backer ground plate extends along a front face of the receiving electrode assembly, wherein the front face is coplanar with the plane formed by the receiving electrode.

4. The system of claim 1, wherein during operation of the system, the transmitting electrode and the receiving electrode are in direct physical contact with the MUT and either electrically non-conductive with the MUT or electrically conductive with the MUT.

5. The system of claim 1, further comprising:
    a signal generator/analyzer coupled with the transmitting electrode and the receiving electrode, the signal generator/analyzer comprising a generator component configured to initiate transmission of a set of electromagnetic signals over a range of frequencies from the transmitting electrode, through the MUT, to the receiving electrode, and an analyzer component configured to detect a change in the set of electromagnetic signals from the transmitting electrode to the receiving electrode; and
    a computing device coupled with the signal generator/analyzer, wherein the computing device is configured to determine a characteristic of the MUT based upon the change in the set of electromagnetic signals from the transmitting electrode to the receiving electrode, wherein determining the characteristic of the MUT comprises: determining a difference in an aspect of the set of electromagnetic signals; comparing the difference in the aspect to a predetermined threshold; and determining the characteristic of the MUT based upon the compared difference.

6. The system of claim 1, wherein the transmitting electrode and the receiving are aligned parallel to one another, and wherein the transmitting surface of the transmitting electrode is larger than the receiving surface of the receiving electrode.

7. The system of claim 1, wherein the electrically non-conducting container has a cylindrical cross-section, rectangular cross-section, or oblong cross-section, taken in a direction perpendicular to a primary axis thereof, and wherein the electrically non-conducting container comprises an inner liner formed of an electrically non-conducting material.

8. The system of claim 1, wherein the electrically non-conducting container includes at least two distinct sections, wherein the transmitting electrode has a diameter larger than an inner diameter of the electrically non-conducting container, and wherein one of the at least two distinct sections comprises a seat for supporting an overhang portion of the transmitting electrode.

9. The system of claim 1, wherein the transmitting electrode assembly and the receiving electrode assembly are shaped to coincide with a cross-sectional shape of the first opening and second opening, respectively, of the electrically non-conducting container.

10. The system of claim 1, wherein the transmitting electrode assembly and the receiving electrode assembly are substantially contained within the electrically non-conducting container.

11. The system of claim 1, wherein the transmitting electrode assembly and the receiving electrode assembly are sized to complement an opening in a soil compaction device.

12. The system of claim 1, wherein the MUT comprises a soil, a granular material, wet concrete, or a liquid including organic or inorganic compounds.

13. The system of claim 1, wherein the transmitting electrode has a diameter that is larger than an inner diameter of the electrically non-conducting container.

14. The system of claim 5, wherein the set of electromagnetic signals are transmitted over a frequency range of approximately 100 kHz to 100 MHz.

15. A method comprising:
placing a material under test (MUT) in a testing system comprising:
an electrically non-conducting container; and
a transmitting electrode assembly,
sealing a bottom of the electrically non-conducting container;
placing a receiving electrode assembly at an end of the electrically non-conducting container over the MUT;
transmitting a set of electromagnetic signals over a range of frequencies from the transmitting electrode assembly, through the MUT to the receiving electrode assembly; and
determining a characteristic of the MUT based upon a change in the set of electromagnetic signals from the transmitting electrode assembly to the receiving electrode assembly.

16. The method of claim 15, further comprising compacting the MUT prior to placing the receiving electrode assembly at the end of the electrically non-conducting container over the MUT.

17. A method of assembling a testing system, the method comprising:
placing a container;
placing a material under test (MUT) in the container including a transmitting electrode, wherein the MUT comprises a soil, a granular material, wet concrete, or a liquid including organic or inorganic compounds;
sealing a bottom of the container; and
placing a receiving electrode at an end of the containers, wherein the transmitting electrode opposes the receiving electrode, and wherein the MUT is contained in the container between the receiving electrode and the transmitting electrode.

18. The method of claim 17, wherein the container is electrically non-conducting, and wherein the receiving electrode is part of a receiving electrode assembly that seals an opposing portion of the container from the bottom of the container such that the MUT is positioned between the receiving electrode and the transmitting electrode.

19. The method of claim 17, wherein the receiving electrode and the transmitting electrode each contact a surface of the MUT without penetrating the surface of the MUT.

\* \* \* \* \*